(12) United States Patent
Ferrone et al.

(10) Patent No.: US 9,296,811 B2
(45) Date of Patent: Mar. 29, 2016

(54) METHODS FOR TREATING A TUMOR USING AN ANTIBODY THAT SPECIFICALLY BINDS HMW-MAA

(75) Inventors: Soldano Ferrone, Boston, MA (US); Xinhui Wang, Boston, MA (US); Elvira Favoino, Casamassima Bari (IT); Ling Yu, Pittsburgh, PA (US); Yangyang Wang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 177 days.

(21) Appl. No.: 13/991,136

(22) PCT Filed: Dec. 1, 2011

(86) PCT No.: PCT/US2011/062943
§ 371 (c)(1),
(2), (4) Date: May 31, 2013

(87) PCT Pub. No.: WO2012/075324
PCT Pub. Date: Jun. 7, 2012

(65) Prior Publication Data
US 2013/0259873 A1    Oct. 3, 2013

Related U.S. Application Data

(60) Provisional application No. 61/419,208, filed on Dec. 2, 2010.

(51) Int. Cl.
| | |
|---|---|
| *A61K 39/395* | (2006.01) |
| *A61K 31/437* | (2006.01) |
| *A61K 45/06* | (2006.01) |
| *C07K 16/18* | (2006.01) |
| *C07K 16/30* | (2006.01) |
| *A61K 39/00* | (2006.01) |

(52) U.S. Cl.
CPC .............. *C07K 16/18* (2013.01); *A61K 31/437* (2013.01); *A61K 39/3955* (2013.01); *A61K 39/39558* (2013.01); *A61K 45/06* (2013.01); *C07K 16/3053* (2013.01); *A61K 2039/505* (2013.01); *C07K 2317/21* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| 2005/0063967 A1* | 3/2005 | Young et al. ............... 424/141.1 |
| 2011/0200608 A1* | 8/2011 | Wang et al. ................ 424/142.1 |

OTHER PUBLICATIONS

Cespedes et al (University of Minnesota Undergraduate Research Presentation, 2010, published Apr. 21, 2010).*
Cespedes et al. (University of Minnesota, poster, 2010, published Apr. 21, 2010).*
Yang et al. (Cancer Research, 2010, 70:5518-5527).*
Flaherty et al. (New England Journal of Medicine, 2010, 363:809-819).*
International Search Report and Written Opinion from patent PCT Application No. PCT/US2011/062943, 9 pages (mailed on Apr. 5, 2012).
Kitago et al., "mRNA Expression and BRAF Mutation in Circulating Melanoma Cells Isolated from Peripheral Blood with High Molecular Weight Melanoma-Associated Antigen-Specific Monoclonal Antibody Beads," Clinical Chemistry 55(4):757-764 (Apr. 2009).
Lin et al., "Polyclonality of BRAF Mutations in Acquired Melanocytic Nevi," *J. Natl. Cancer. Inst.* 101:1423-1427 (Oct. 2009).
Yu et al., "The CSPG4-specific Monoclonal Antibody Enhances and Prolongs the Effects of the BRAF Inhibitor in Melanoma Cells," *Immunol. Res.* 50(2-3):294-302 (Aug. 2011)(Abstract only).

* cited by examiner

*Primary Examiner* — Sean Aeder
*Assistant Examiner* — Julie Wu
(74) *Attorney, Agent, or Firm* — Klarquist Sparkman, LLP

(57) ABSTRACT

Combinations of agents that have a synergistic effect for the treatment of a tumor are disclosed herein. These combinations of agents can be used to treat tumors, wherein the cells of the cancer express a mutated BRAF. Methods are disclosed for treating a subject diagnosed with a tumor that expresses a mutated BRAF. The methods include administering to the subject (1) a therapeutically effective amount of an antibody or antigen binding fragment thereof that specifically binds high molecular weight melanoma associated antigen (HMW-MAA), also known as CSPG4; and (2) a therapeutically effective amount of a BRAF inhibitor. In some embodiments, the tumor is melanoma. In some embodiments the method includes selecting a subject with primary or secondary resistance to a BRAF inhibitor. In further embodiments, treating the tumor comprises decreasing the metastasis of the tumor. In additional embodiments, the BRAF inhibitor comprises PLX4032 or PLX4720.

17 Claims, 14 Drawing Sheets

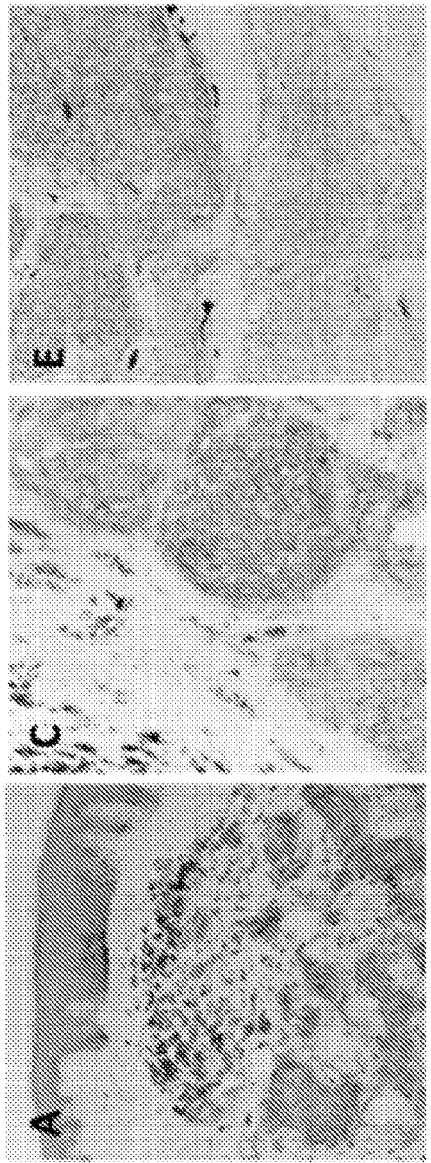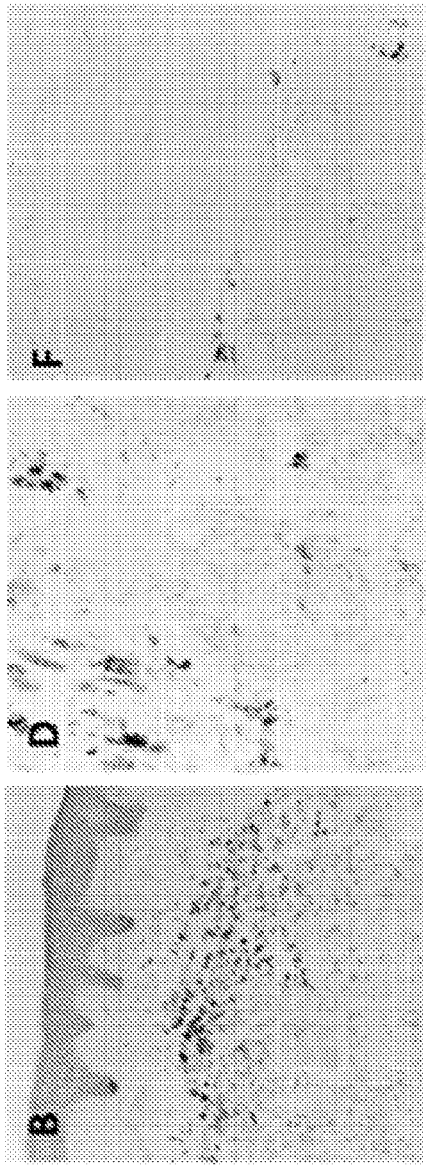

SEQUENCE LISTING

```
<160> NUMBER OF SEQ ID NOS: 7

<210> SEQ ID NO 1
<211> LENGTH: 327
<212> TYPE: PRT
<213> ORGANISM: Homo sapiens

<400> SEQUENCE: 1

Glu Gln Met Arg Glu Glu Pro Glu Ala Ala Tyr Arg Leu Ile Gln Gly
1               5                   10                  15

Pro Gln Tyr Gly His Leu Leu Val Gly Gly Arg Pro Thr Ser Ala Phe
            20                  25                  30

Ser Gln Phe Gln Ile Asp Gln Gly Glu Val Val Phe Ala Phe Thr Asn
        35                  40                  45

Phe Ser Ser His Asp His Phe Arg Val Leu Ala Leu Ala Arg Gly
    50                  55                  60

Val Asn Ala Ser Ala Val Val Asn Val Thr Val Arg Ala Leu Leu His
65                  70                  75                  80

Val Trp Ala Gly Gly Pro Trp Pro Gln Gly Ala Thr Leu Arg Leu Asp
                85                  90                  95

Pro Thr Val Leu Asp Ala Gly Glu Leu Ala Asn Arg Thr Gly Ser Val
            100                 105                 110

Pro Arg Phe Arg Leu Leu Glu Gly Pro Arg His Gly Arg Val Val Arg
        115                 120                 125

Val Pro Arg Ala Arg Thr Glu Pro Gly Gly Ser Gln Leu Val Glu Gln
    130                 135                 140

Phe Thr Gln Gln Asp Leu Glu Asp Gly Arg Leu Gly Leu Glu Val Gly
145                 150                 155                 160

Arg Pro Glu Gly Arg Ala Pro Gly Pro Ala Gly Asp Ser Leu Thr Leu
                165                 170                 175

Glu Leu Trp Ala Gln Gly Val Pro Pro Ala Val Ala Ser Leu Asp Phe
            180                 185                 190

Ala Thr Glu Pro Tyr Asn Ala Ala Arg Pro Tyr Ser Val Ala Leu Leu
        195                 200                 205

Ser Val Pro Glu Ala Ala Arg Thr Glu Ala Gly Lys Pro Glu Ser Ser
    210                 215                 220
```

```
Thr Pro Thr Gly Glu Pro Gly Pro Met Ala Ser Ser Pro Glu Pro Ala
225                 230                 235                 240

Val Ala Lys Gly Gly Phe Leu Ser Phe Leu Glu Ala Asn Met Phe Ser
            245                 250                 255

Val Ile Ile Pro Met Cys Leu Val Leu Leu Leu Ala Leu Ile Leu
        260                 265                 270

Pro Leu Leu Phe Tyr Leu Arg Lys Arg Asn Lys Thr Gly Lys His Asp
        275                 280                 285

Val Gln Val Leu Thr Ala Lys Pro Arg Asn Gly Leu Ala Gly Asp Thr
        290                 295                 300

Glu Thr Phe Arg Lys Val Glu Pro Gly Gln Ala Ile Pro Leu Thr Ala
305                 310                 315                 320

Val Pro Gly Gln Leu Phe Pro
                325

<210> SEQ ID NO 2
<211> LENGTH: 983
<212> TYPE: DNA
<213> ORGANISM: Homo sapiens

<400> SEQUENCE: 2
gggagcagat gagggaggag ccagaggcag cataccgcct catccaggga ccccagtatg      60
ggcatctcct ggtgggcggg cggcccacct cggccttcag ccaattccag atagaccagg    120
gcgaggtggt ctttgccttc accaacttct cctcctctca tgaccacttc agagtcctgg    180
cactggctag gggtgtcaat gcatcagccg tagtgaacgt cactgtgagg gctctgctgc    240
atgtgtgggc aggtgggcca tggccccagg gtgccaccct gcgcctggac cccaccgtcc    300
tagatgctgg cgagctggcc aaccgcacag gcagtgtgcc gcgcttccgc ctcctggagg    360
gaccccggca tggccgcgtg gtccgcgtgc ccgagccag acggagccc ggggcagcc     420
agctggtgga gcagttcact cagcaggacc ttgaggacgg gaggctgggg ctggaggtgg    480
gcaggccaga ggggagggcc cccggccccg caggtgacag tctcactctg gagctgtggg    540
cacagggcgt cccgcctgct gtggcctccc tggactttgc cactgagcct acaatgctg    600
cccggccta cagcgtggcc ctgctcagtg tccccgaggc cgcccggacg aagcaggga    660
agccagagag cagcaccccc acaggcgagc caggccccat ggcatccagc cctgagcccg    720
ctgtggccaa gggaggcttc ctgagcttcc ttgaggccaa catgttcagc gtcatcatcc    780
ccatgtgcct ggtacttctg ctcctggcgc tcatcctgcc cctgctcttc tacctccgaa    840
aacgcaacaa gacgggcaag catgacgtcc aggtcctgac tgccaagccc cgcaacggcc    900
tggctggtga caccgagacc tttcgcaagg tggagccagg ccaggccatc ccgctcacag    960
ctgtgcctgg ccagttattt cca                                            983

<210> SEQ ID NO 3
<211> LENGTH: 118
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
 50                      55                  60

Gln Gly Arg Val Thr Ile Thr Ala Asp Glu Ser Thr Ser Thr Ala Tyr
 65                      70                  75                  80

Met Glu Leu Ser Ser Leu Arg Ser Asp Asp Thr Ala Val Tyr Tyr Cys
                 85                  90                  95

Ala Arg Ala Leu Asp Pro Ile Thr Phe Asp Ser Trp Gly Gln Gly Thr
                100                 105                 110

Leu Val Thr Val Ser Arg
                115

<210> SEQ ID NO 4
<211> LENGTH: 110
<212> TYPE: PRT
<213> ORGANISM: Homo sapiens

<400> SEQUENCE: 4

Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
                 20                  25                  30

Trp Tyr Gln Gln Lys Pro Gly Gln Ala Pro Val Leu Val Ile Tyr Gly
             35                  40                  45

Lys Asn Asn Arg Pro Ser Gly Ile Pro Asp Arg Phe Ser Gly Ser Ser
 50                      55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Arg Asp Ser Ser Gly Asn His Val
                 85                  90                  95

Val Phe Gly Gly Gly Thr Lys Leu Thr Val Leu Gly Arg Ser
                100                 105                 110

<210> SEQ ID NO 5
<211> LENGTH: 433
<212> TYPE: PRT
<213> ORGANISM: Pseudomonas aeruginosa

<400> SEQUENCE: 5

Pro Arg Arg Glu Lys Arg Trp Ser Glu Trp Ala Ser Gly Lys Val Leu
 1               5                  10                  15

Cys Leu Leu Asp Pro Leu Asp Gly Val Tyr Asn Tyr Leu Ala Gln Gln
                 20                  25                  30

Arg Cys Asn Leu Asp Asp Thr Trp Glu Gly Lys Ile Tyr Arg Val Leu
             35                  40                  45

Ala Gly Asn Pro Ala Lys His Asp Leu Asp Ile Lys Pro Thr Val Ile
 50                      55                  60

Ser His Arg Leu His Phe Pro Glu Gly Gly Ser Leu Ala Ala Leu Thr
 65                  70                  75                  80

Ala His Gln Ala Cys His Leu Pro Leu Glu Thr Phe Thr Arg His Arg
                 85                  90                  95

Gln Pro Arg Gly Trp Glu Gln Leu Glu Gln Cys Gly Tyr Pro Val Gln
                100                 105                 110

Arg Leu Val Ala Leu Tyr Leu Ala Ala Arg Leu Ser Trp Asn Gln Val
            115                 120                 125
```

```
Asp Gln Val Ile Arg Asn Ala Leu Ala Ser Pro Gly Ser Gly Gly Asp
        130                 135                 140

Leu Gly Glu Ala Ile Arg Glu Gln Pro Glu Gln Ala Arg Leu Ala Leu
145                 150                 155                 160

Thr Leu Ala Ala Ala Glu Ser Glu Arg Phe Val Arg Gln Gly Thr Gly
                165                 170                 175

Asn Asp Glu Ala Gly Ala Asn Ala Asp Val Val Ser Leu Thr Cys
                180                 185                 190

Pro Val Ala Ala Gly Glu Cys Ala Gly Pro Ala Asp Ser Gly Asp Ala
                195                 200                 205

Leu Leu Glu Arg Asn Tyr Pro Thr Gly Ala Glu Phe Leu Gly Asp Gly
        210                 215                 220

Gly Asp Val Ser Phe Ser Thr Arg Gly Thr Gln Asn Trp Thr Val Glu
225                 230                 235                 240

Arg Leu Leu Gln Ala His Arg Gln Leu Glu Arg Gly Tyr Val Phe
                245                 250                 255

Val Gly Tyr His Gly Thr Phe Leu Glu Ala Ala Gln Ser Ile Val Phe
                260                 265                 270

Gly Gly Val Arg Ala Arg Ser Gln Asp Leu Asp Ala Ile Trp Arg Gly
        275                 280                 285

Phe Tyr Ile Ala Gly Asp Pro Ala Leu Ala Tyr Gly Tyr Ala Gln Asp
        290                 295                 300

Gln Glu Pro Asp Ala Arg Gly Arg Ile Arg Asn Gly Ala Leu Leu Arg
305                 310                 315                 320

Val Tyr Val Pro Arg Ser Ser Leu Pro Gly Phe Tyr Arg Thr Ser Leu
                325                 330                 335

Thr Leu Ala Ala Pro Glu Ala Leu Gly Glu Val Glu Arg Leu Ile Gly
                340                 345                 350

His Pro Leu Pro Leu Arg Leu Asp Ala Ile Thr Gly Pro Glu Glu Glu
            355                 360                 365

Gly Gly Arg Leu Glu Thr Ile Leu Gly Trp Pro Leu Ala Glu Arg Thr
370                 375                 380

Val Val Ile Pro Ser Ala Ile Pro Thr Asp Pro Arg Asn Val Gly Gly
385                 390                 395                 400

Asp Leu Asp Pro Ser Ser Ile Pro Asp Lys Glu Gln Ala Ile Ser Ala
                405                 410                 415

Leu Pro Asp Tyr Ala Ser Gln Pro Gly Lys Pro Pro Arg Glu Asp Leu
                420                 425                 430

Lys

<210> SEQ ID NO 6
<211> LENGTH: 4
<212> TYPE: PRT
<213> ORGANISM: Pseudomonas aeruginosa

<400> SEQUENCE: 6

Lys Asp Glu Leu
1

<210> SEQ ID NO 7
<211> LENGTH: 4
<212> TYPE: PRT
<213> ORGANISM: Pseudomonas aeruginosa
```

```
<400> SEQUENCE: 7

Arg Glu Asp Leu
1
```

METHODS FOR TREATING A TUMOR USING AN ANTIBODY THAT SPECIFICALLY BINDS HMW-MAA

CROSS REFERENCE TO RELATED APPLICATIONS

PRIORITY CLAIM

This is the U,S. National Stage of International Application No. PCT/US2011/062943, filed Dec. 1, 2011, which was published in English under PCT Article 21(2), which in turn claims the benefit of U.S. Provisional Application No. 61/419,208, filed Dec. 2, 2010, which is incorporated by reference herein.

FIELD

This application relates to the treatment of cancer, specifically to the use of a combination of agents that include an antibody that specifically binds high molecular weight melanoma associated antigen (HMW-MAA) and a BRAF inhibitor to treat cancer, such as melanoma.

BACKGROUND

Melanoma is a malignant tumor of melanocytes that are predominately found in skin, but can also be found in the bowel and eye. Although melanoma is not the most common form of skin cancer, it causes the majority of skin cancer related deaths. Melanoma incidence and mortality rates in fair-skinned populations are increasing worldwide. Approximately 160,000 cases of malignant melanoma are diagnosed in the world each year. Current treatments include surgical removal of the tumor, adjuvant treatment, chemotherapy, immunotherapy and radiation therapy.

RAF protein kinases are key components of signal transduction pathways by which specific extracellular stimuli elicit precise cellular responses in mammalian cells. Activated cell surface receptors activate ras/rap proteins at the inner aspect of the plasma-membrane which in turn recruit and activate Raf proteins. Activated RAF proteins phosphorylate and activate the intracellular protein kinases MEK1 and MEK2. In turn, activated MEKs catalyze phosphorylation and activation of p42/p44 mitogen-activated protein kinase (MAPK). Several cytoplasmic and nuclear substrates of activated MAPK are known that directly or indirectly contribute to the cellular response to environmental change. Three distinct genes have been identified in mammals that encode Raf proteins: ARAF, BRAF and CRAF (also known as RAF-1).

Inhibitors of RAF kinases have been suggested for use in disruption of tumor cell growth and in the treatment of cancers, such as histiocytic lymphoma, adenocarcinoma, small cell lung cancer, melanoma and pancreatic and breast carcinoma. Specific inhibitors of BRAF mutants, such as V600E (BRAF$^{V600E}$ mutant) are known and have been used for the treatment of cancer. However, some subjects are refractory to treatment with BRAF inhibitors. Furthermore, some subjects develop secondary resistance to BRAF inhibitors, such that regression induced by a BRAF inhibitor is only temporary. Thus, a need remains for agents that augment the effect of BRAF inhibitors, such as a combination of agents of use for treating cancer and for inhibiting secondary resistance to a BRAF inhibitor.

SUMMARY

Combinations of agents that have a synergistic effect for the treatment of cancer are disclosed herein. These combinations of agents can be used to treat cancers, wherein the cells of the cancer express a mutated BRAF. The compositions include a therapeutically effective amount of a BRAF inhibitor.

Methods are disclosed for treating a subject diagnosed with a tumor that expresses a mutated BRAF. The methods include administering to the subject (1) a therapeutically effective amount of an antibody or antigen binding fragment thereof that specifically binds high molecular weight melanoma associated antigen (HMW-MAA), also known as CSPG4; and (2) a therapeutically effective amount of a BRAF inhibitor.

In some embodiments, the cells in the tumor can have a BRAF V600E mutation. In further embodiments, the tumor is melanoma. In additional embodiments, treating the tumor comprises decreasing the metastasis of the tumor. In additional embodiments, the BRAF inhibitor is vemurafenib (also known as PLX4032). The disclosed methods are of use to treat a subject that has primary or secondary resistance to the BRAF inhibitor.

In some embodiments, the methods comprise administering to the subject a therapeutically effective amount of an antibody or antigen binding fragment thereof that specifically binds HMW-MAA (CSPG4). For example, the antibody is monoclonal antibody 225.28 or monoclonal antibody 763.74, a humanized form thereof or an antigen binding fragment thereof. In other examples, the antibody includes one, two or three of the heavy chain CDRs of the amino acid sequence set forth as SEQ ID NO: 3 and/or one, two or three of the light chain CDRs of the amino acid sequence set forth as SEQ ID NO: 4. In some examples the methods comprise the use of an scFv that specifically binds HMW-MAA (CSPG4).

The foregoing and other objects, features, and advantages of the invention will become more apparent from the following detailed description, which proceeds with reference to the accompanying figures.

BRIEF DESCRIPTION OF THE DRAWINGS

(FIG. 5A) Representative FACS analysis of CSPG4 expression by melanoma cell lines using CSPG4-specific C21 and PE-conjugated anti-human IgG. 119 was used as an isotype control. (FIG. 5B) A panel of melanoma cell lines bound by C21. *Percentage of $CSPG4^+$ cells. MFI: mean fluorescence intensity. The top section (1520, 836, Colo38, M21, MEL526, MV3, KS-MEL-28, SK-MEL-37, and WM1158) are established melanoma cell lines; The bottom section (MeI-JR(pre), MEL-JR(post), Mel-KD(pre), and Mel-KD(post)) are patient-derived human melanoma cell lines; pre: before vemurafenib (PLX4032) treatment, post: after vemurafenib (PLX4032) treatment.

FIG. 6A-6F. Digital images of immunohistochemical staining of frozen sections of human melanocytic lesions with C21. Benign pigmented nevus (FIG. 6A), primary melanoma (FIG. 6C), and metastatic melanoma (FIG. 6E) exhibited homogeneous cytoplasmic and cytoplasmic membrane staining with C21. Corresponding sections of nevus (FIG. 6B), primary (FIG. 6D), and metastatic melanoma (FIG. 6F) exhibited an absence of staining with 119 (negative control).

(FIG. 10A) Human melanoma cells, M21, were injected s.c. ($2 \times 10^6$/mouse) into 30 mice (day 0). By day 7, tumors were measurable, and mice were divided into six groups (5 mice/group) using a stratified randomization strategy. These groups included: vemurafenib—received vemurafenib (25 mg/kg) orally every day for 13 days; C21—received an intravenous (i.v.) injection of C21 (1 mg/mouse) twice a week for 2 weeks; 119—received an i.v. injection of 119 (1 mg/mouse) twice a week for 2 weeks, Vemurafenib+C21—received vemurafenib orally, plus an i.v. injection of C21 (1 mg/mouse) twice a week for 2 weeks, Vemurafenib+119—received vemurafenib orally, plus an i.v. injection of 119 (1 mg/mouse) twice a week for 2 weeks, untreated—no treatment was received. Primary tumor volumes of the vemurafenib+C21 group were found to be significantly less than that of the vemurafenib or C21 treatment groups alone (p<0.001 in both cases). (FIG. 10B) On day 35, mice were sacrificed and primary tumors were fixed in 10% formalin and paraffin-embedded. IHC staining for pHistone H3, an indicator of mitotic cells was performed. Treatment with vemurafenib+C21 versus either agent alone was p=0.003 and p=0.001, respectively. (FIG. 10C) Two tumor lysates from each group were analyzed by immunoblotting as indicated. Calnexin and β-actin were used as loading controls. Levels of p-FAK, p-ERK1/2, and p-AKT were lower, while levels of cleaved PARP and caspase 7, were higher, in tumors treated with vemurafenib+C21 than in tumors treated by either agent alone.

SEQUENCE LISTING

Figure 1:
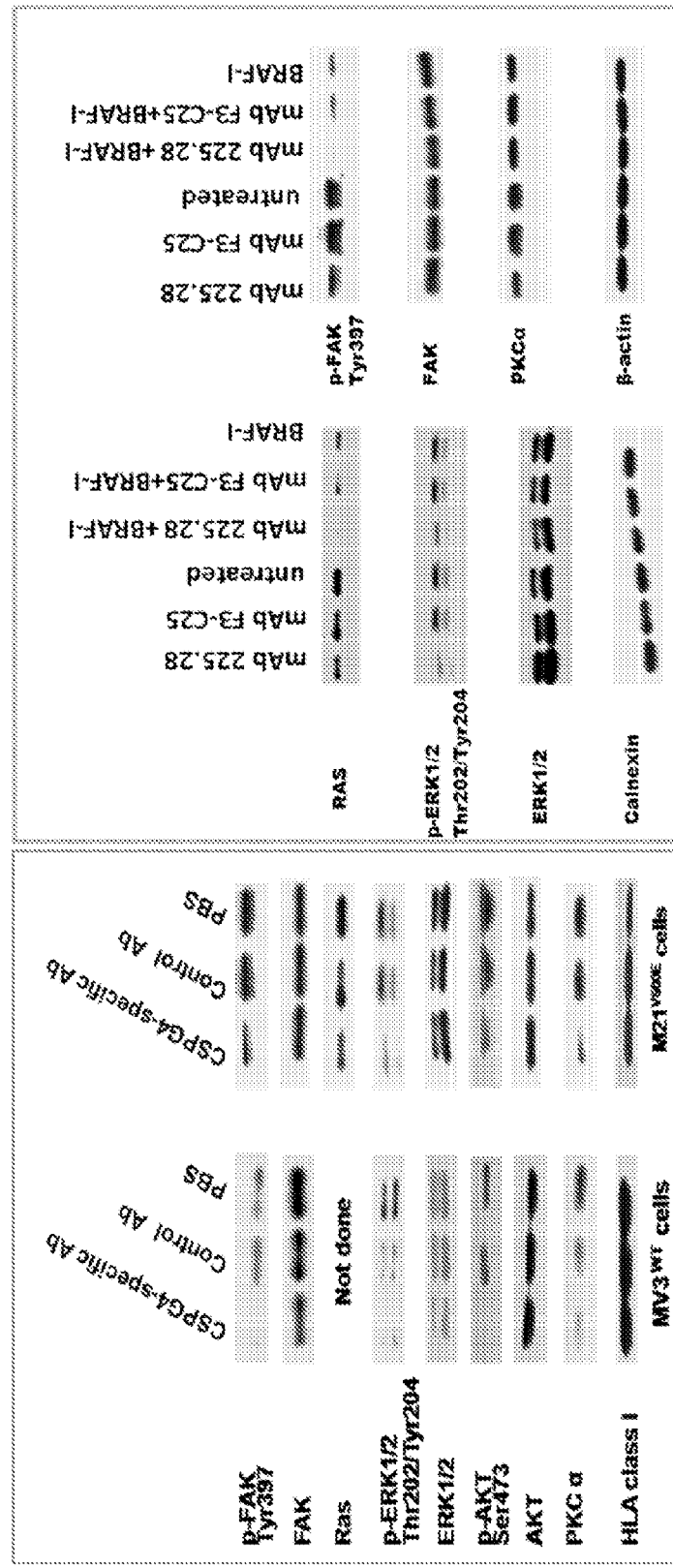
FIG. 1A. Effect of anti-HMW-MAA (CSPG4)-mAb on multiple signaling pathways in vivo. The human melanoma cell lines MV3 (BRAF wild type) and M21 (BRAF$^{V600E}$ mutant) were incubated with either the anti-CSPG4-mAb, the control mAb, or PBS for 48 hours at 37° C. Cell lysate were tested in western blot with anti-phosphorylated (p)-FAK, FAK, p-AKT, AKT, Ras, p-ERK1/2 ERK1/2, and PKCα antibodies. HLA class I heavy chain (HLA class I) was used as the loading control.
FIG. 1B. Effect of anti-HMW-MAA (CSPG4)-mAb in combination with BRAF-I on multiple signaling pathways in vitro. The human melanoma cell M21R was serum starved for 3 days then seeded at the concentration of $1.0 \times 10^5$ per well in a 6-well plate in RPMI 1640 medium without serum and incubated with CSPG4-specific mAb 225.28 (0.25 mg/mL), the control mAb F3-C25, or untreated in presence of BRAF inhibitor PLX4720 (5 μM) for 72 hours at 37° C. Cell lysate were tested in western blot with anti-RAS, c-RAF, phosphorylated (p)-MEK, p-ERK1/2h, ERK1/2, (p)-FAK (Tyr397), FAK, and PKCα mAbs. Calnexin and β-actin was used as the loading control.

The Sequence Listing is submitted as an ASCII text file [8123-88254-02_Sequence_Listing.txt, May 31, 2013, 10.5 KB] which is incorporated by reference herein.

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is an amino acid sequence of HMW-MAA.

SEQ ID NO: 2 is an exemplary nucleic acid sequence encoding HMW-MAA.

SEQ ID NO: 3 is an amino acid sequence of the heavy chain of a monoclonal antibody that specifically binds HMW-MAA.

SEQ ID NO: 4 is an amino acid sequence of the light chain of a monoclonal antibody that specifically binds HMW-MAA.

SEQ ID NO: 5 is the amino acid sequence of *Pseudomonas* exotoxin.

SEQ ID NOs: 6-7 are variants of *Pseudomonas* exotoxin.

DETAILED DESCRIPTION

Disclosed herein are methods for treating a tumor in a subject. The methods include selecting a subject with a BRAF mutation, and administering to the subject a therapeutically effective amount of 1) an antibody that specifically binds high molecular weight melanoma associate antigen (HMW-MAA) (CSPG4); and 2) a BRAF inhibitor. The use of a combination of an antibody that specifically binds HMW-MAA and a BRAF inhibitor for the treatment of cancer provides an unexpectedly superior result for the treatment of a tumor, wherein cells in the tumor comprise a BRAF mutation. In some embodiments, the tumor is a melanoma. In other embodiments, the BRAF mutation is a V600E mutation. In additional embodiments, the subject has resistance to the BRAF inhibitor. In some specific non-limiting examples, the BRAF inhibitor is PLX4032 or PLX4720.

Disclosed herein are methods to treat a subject diagnosed with a tumor, such as tumor that expresses HMW-MAA. In some embodiments, methods are provided for treating a melanoma. Melanoma includes spreading melanoma, nodular melanoma, acral lentiginous melanoma, and lentigo maligna (melanoma). However, the methods disclosed herein can also be used to treat other cancers, such breast cancer, prostate cancer, ovarian cancer, colon cancer, stomach cancer, pancreatic cancer, glioma, chordoma, chondrosarcoma, glioma or a squamous cell carcinoma. Squamous cell carcinomas include, but are not limited to head and neck squamous cell carcinoma, and squamous cell cancers of the skin, lung, prostate, esophagus, vagina and cervix.

The disclosed methods can also be used to prevent metastasis or decrease the number of micrometastases, such as micrometastases to regional lymph nodes.

Pharmaceutical compositions are also provided that include a therapeutically effective amount of an antibody that specifically binds HMW-MAA and a therapeutically effective amount of a BRAF inhibitor. In specific, non-liming examples, the BRAF inhibitor is PLX4032 or PLX4720. These compositions are of use for treating tumors.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and specifically binds an epitope of an antigen, such as HMW-MAA or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds HMW-MAA will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds HMW-MAA.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen, such as HMW-MAA with a high affinity and does not significantly bind other unrelated antigens.

BRAF: A member of the Raf kinase family of serine/threonine-specific protein kinases. This protein plays a role in regulating the MAP kinase/ERKs signaling pathway, which affects cell division, differentiation, and secretion. B-Raf transduces cellular regulatory signals from Ras to MEK in vivo. BRAF is also referred to as v-raf murine sarcoma viral oncogene homolog B1.

BRAF Mutant: A mutated form of BRAF that has increased basal kinase activity relative to the basal kinase activity of wild type BRAF is also an activated form of BRAF. More than 30 mutations of the BRAF gene that are associated with human cancers have been identified. The frequency of BRAF mutations in melanomas and nevi are 80%. In 90% of the cases, a Glu for Val substitution at position 600 (referred to as V600E) in the activation segment has been found in human cancers. This mutation is observed in papillary thyroid cancer, colorectal cancer and melanoma. Other mutations which have been found are R462I, I463S, G464E, G464V, G466A, G466E, G466V, G469A, G469E, N581S, E585K, D594V, F595L, G596R, L597V, T599I, V600D, V600K, V600R, K601E or A728V. Most of these mutations are clustered to two regions: the glycine-rich P loop of the N lobe and the activation segment and flanking regions. A mutated form of BRAF that induces focus formation more efficiently than wild type BRAF is also an activated form of BRAF.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a melanoma or another tumor. In one embodiment, a chemotherapeutic agent is a radioactive compound. One of skill in the art can readily identify a chemotherapeutic agent (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds HMW-MAA or an antigen binding fragment thereof, used in combination with a BRAF inhibitor, such as a chemical compound.

Decrease in survival: As used herein, "decrease in survival" refers to a decrease in the length of time before death of a patient, or an increase in the risk of death for the patient. A decrease in survival also can refer to a decrease in the average time to death in a group, such as a group of patients diagnosed with a cancer, such as melanoma.

Diagnosing: Refers to the process of identifying the nature or cause of a disease or disorder.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-HMW-MAA antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as HMW-MAA, BRAF.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

High molecular weight melanoma associate antigen (HMW-MAA: A human melanoma-associated chondroitin sulfate proteoglycan that plays a role in stabilizing cell-substratum interactions during early events of melanoma cell spreading on endothelial basement membranes. This molecule, also known as CSPG4 is an integral membrane chondroitin sulfate proteoglycan expressed by human malignant melanoma cells.

Inhibitor: As used herein, an "inhibitor" refers to any compound that is capable of reducing or altering the expression or activity of a target molecule. In some embodiments, the inhibitor is an inhibitor of BRAF.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Melanoma: A form of cancer that originates in melanocytes (cells that make the pigment melanin). Melanocytes are found primarily in the skin, but are also present in the bowel and eye. As used herein, "melanoma" refers to any stage of melanoma, or any subtype of melanoma, such as superficial spreading melanoma, nodular melanoma, acral lentiginous melanoma, lentigo maligna, melanoma-in-situ, mucosal melanoma and uveal melanoma. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma and uveal melanoma.

Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis. When melanomas have spread to the lymph nodes, one of the most important factors is the number of nodes with malignancy. The extent of malignancy within a node is also important; micrometastases in which malignancy is only microscopic have a more favorable prognosis than macrometastases. When there is distant metastasis, the five year survival rate is less than 10 percent; the median survival is 6 to 12 months. Metastases to skin and lungs have a better prognosis. Metastases to brain, bone and liver are associated with a worse prognosis.

Melanoma can be staged as follows:
Stage 0: Melanoma in Situ (Clark Level I), 100% Survival
Stage I/II: Invasive Melanoma, 85-95% Survival
  T1a: Less than 1.00 mm primary, w/o Ulceration, Clark Level II-III
  T1b: Less than 1.00 mm primary, w/Ulceration or Clark Level IV-V
  T2a: 1.00-2.00 mm primary, w/o Ulceration
Stage II: High Risk Melanoma, 40-85% Survival
  T2b: 1.00-2.00 mm primary, w/ Ulceration
  T3a: 2.00-4.00 mm primary, w/o Ulceration
  T3b: 2.00-4.00 mm primary, w/ Ulceration
  T4a: 4.00 mm or greater primary w/o Ulceration
  T4b: 4.00 mm or greater primary w/ Ulceration
Stage III: Regional Metastasis, 25-60% Survival
  N1: Single Positive Lymph Node
  N2: 2-3 Positive Lymph Nodes OR Regional Skin/In-Transit Metastasis
  N3: 4 Positive Lymph Nodes OR Lymph Node and Regional Skin/In Transit Metastases
Stage IV: Distant Metastasis, 9-15% Survival
  M1a: Distant Skin Metastasis, Normal lactate dehydrogenase (LDH)
  M1b: Lung Metastasis, Normal LDH
  M1c: Other Distant Metastasis OR Any Distant Metastasis with Elevated LDH Metastasis: Refers to the spread of cancer cells from the original tumor to other sites in the body.

Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized and fully human monoclonal antibodies. As used herein a monoclonal antibody includes antibody fragments, such as, but not limited to scFv, Fv, dsRv, or Fab.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells (such as cancer cells), but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as discussed below, but generally refers to the subset of constitutional alterations that have arisen within the past few generations in a kindred and that are not widely disseminated in a population group.

In some embodiments, a mutation in BRAF refers to a nucleotide substitution in the BRAF gene or cDNA, or an amino acid substitution in the BRAF protein.

Neoplasia, malignancy, cancer or tumor: The result of abnormal and uncontrolled growth of cells. A neoplasm is an abnormal growth of tissue or cells that results from excessive cell division. Neoplastic growth can produce a tumor. malignancy, cancer and tumor are often used interchangeably. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, a tumor is melanoma, breast cancer, prostate cancer, glioma or a squamous cell carcinoma, such as head and neck cancer.

Nevi: Melanocytic lesions that can be considered regional melanocytic hyperplasias. The term "nevi" includes all types of nevi, such as congenital nevi, acquired nevi, intradermal nevi, compound nevi, dysplastic nevi, atypical nevi, and junctional nevi.

Nevus: The term "nevus" encompasses one or more nevi, including one or more in vivo nevi cells and one or more in vitro nevi cells. A "nevus" also encompasses one or more melanocytic lesions that can be considered regional melanocytic hyperplasias. The term "nevus" as used herein includes all types of nevi, such as congenital nevi, acquired nevi, intradermal nevi, compound nevi, dysplastic nevi, atypical nevi, and junctional nevi.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Patient: As used herein, the term "patient" includes human and non-human animals. The preferred patient for treatment is a human.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell.

Polymorphism: Variant in a sequence of a gene, or any genomic sequence, usually carried from one generation to another in a population. Polymorphisms can be those variations (nucleotide sequence differences) that, while having a different nucleotide sequence, produce functionally equivalent gene products, such as those variations generally found between individuals, different ethnic groups, and geographic locations. The term polymorphism also encompasses variations that produce gene products with altered function, i.e., variants in the gene sequence that lead to gene products that are not functionally equivalent. This term also encompasses variations that produce no gene product, an inactive gene product, a truncated gene product, or increased or increased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNAses, a change in the availability of a site for cleavage by a restriction endonuclease, either the formation of a new site, or lose of a site, and so forth).

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown in the following table:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease (such as a tumor, for example, metastatic melanoma) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Prognosis: The likelihood of the clinical outcome for a subject afflicted with a specific disease or disorder. With regard to cancer, the prognosis is a representation of the likelihood (probability) that the subject will survive (such as for one, two, three, four or five years) and/or the likelihood (probability) that the tumor will metastasize. A "poor prognosis" indicates a greater than 50% chance that the subject will not survive to a specified time point (such as one, two, three, four or five years), and/or a greater than 50% chance that the tumor will metastasize. In several examples, a poor prognosis indicates that there is a greater than 60%, 70%, 80%, or 90% chance that the subject will not survive and/or a greater than 60%, 70%, 80% or 90% chance that the tumor will metastasize. Conversely, a "good prognosis" indicates a greater than 50% chance that the subject will survive to a specified time point (such as one, two, three, four or five years), and/or a greater than 50% chance that the tumor will not metastasize. In several examples, a good prognosis indicates that there is a greater than 60%, 70%, 80%, or 90% chance that the subject will survive and/or a greater than 60%, 70%, 80% or 90% chance that the tumor will not metastasize.

Proliferation: One or more cellular events that result in cell growth. Proliferation includes any of a number of growth activities including increase in the number of cells, increase in the rate of cell division, increase in the number of cell divisions, increase in the size of a cell, change in cellular differentiation, transformation to a malignant state, metastatic transformation, change in cell cycle phase to a more mitotically active cell cycle phase (e.g., S phase), or a combination of two or more of those activities. Cell growth (either in vitro or in vivo) can be a hyper-proliferative condition, such as is characteristic of certain disorders or diseases, for instance neoplasia or tumor formation.

Inhibiting proliferation includes any of a number of anti-growth activities that reduce or even eliminate the ability of a cell to proliferate. Inhibiting proliferation includes, for instance, decreasing cell number, decreasing colony forming ability, decreasing the rate of cell division, decreasing the number of cell divisions, stopping cell division, inducing apoptosis, inducing senescence, inducing quiescence, changing cell cycle phase to a less mitotically active cell cycle phase, decreasing cellular de-differentiation, preventing transformation to a malignancy, decreasing malignant potential, decreasing metastatic ability or potential or a combination of two or more of those activities.

Resistance: The lack of response of a disease, such as a cancer, to a therapeutic agent. In some embodiment, the agent is a BRAF inhibitor. Primary resistance is the lack of a response to a therapeutic agent upon initial treatment with the agent. Secondary resistance is the lack of a response to a therapeutic agent, wherein the cancer in the subject is initially susceptible to treatment with the agent. Resistance of a cancer to an agent can be measured by an increase in tumor burden, an increase in the number of metastases, or an increase in the amount of a tumor marker present in the subject.

Sample: A biological specimen containing genomic DNA, RNA, protein, or combinations thereof, obtained from a subject. Examples include, but are not limited to, peripheral blood, urine, saliva, tissue biopsy (such as skin tissue), surgical specimen, and autopsy material. In one example, a sample includes a biopsy of a melanoma tumor or a sample of normal tissue, such as skin tissue (from a subject not afflicted with a known disease or disorder, such as a cancer-free subject).

Somatic mutation: An acquired mutation that occurs in a somatic cell (as opposed to a germ cell).

Subject: Living multi-cellular vertebrate organisms, a category that includes both human and non-human mammals. In some embodiments, the subject is a human subject.

Therapeutic agent: A chemical compound, small molecule, or other composition, such as an antisense compound, antibody, peptide or nucleic acid molecule capable of inducing a desired therapeutic or prophylactic effect when properly administered to a subject. For example, therapeutic agents for melanoma include agents that prevent or inhibit development or metastasis of melanoma. In some embodiments, the therapeutic agent is an inhibitor of BRAF.

Therapy: The mode of treatment or care of a patient. In some cases, therapy refers to administration of a therapeutic agent. In some embodiments herein, therapy includes administration of a BRAF inhibitor. In other examples, therapy includes surgery, such as surgical resection of a melanoma tumor, chemotherapy, radiation therapy, or any combination thereof.

Therapeutically effective amount: A quantity of an agent sufficient to achieve a desired effect in a subject or a cell being treated. For instance, this can be the amount necessary to inhibit or to measurably reduce B-Raf activity in a nevi or to inhibit melanoma proliferation. A therapeutically effective amount of an agent may be administered in a single dose, or in several doses, for example daily or more often, during a course of treatment. However, the effective amount will be dependent on the particular agent applied, the subject being treated, the severity and type of the affliction, and the manner of administration.

Treating: Includes inhibiting or preventing the partial or full development or progression of a disease or medical condition or abnormal biological state in a subject, for example in a person who is known to have a predisposition to or to be at risk for the disease or medical condition or abnormal biological state, or a cell or a lesion, for instance a nevus or a melanoma. Furthermore, "treating" refers to a therapeutic intervention that ameliorates at least one sign or symptom of a disease or pathological condition, or interferes with a pathophysiological process, after the disease or pathological condition has begun to develop. The therapeutic intervention can be prophylactic inhibition of a disease or medical condition or biological state, and therapeutic interventions to alter the natural course of an untreated disease process or medical condition or a biological state, such as a tumor growth. The therapeutic intervention can be surgical, including but not limited to cryosurgery or ablation, such as laser ablation, and administration of agents, systemically, regionally, or topically or locally.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Antibodies that Specifically Bind HMW-MAA, Antigen Binding Fragments and Immunotoxins The methods disclosed herein can utilize monoclonal antibodies and functional fragments thereof that specifically bind HMW-MAA, also known as CSPG4. In one example, HMW-MAA has an amino acid sequence set forth as:

(SEQ ID NO: 1)

```
EQMREEPEAA YRLIQGPQYG HLLVGGRPTS AFSQFQIDQG EVVFAFTNFS SSHDHFRVLA

LARGVNASAV VNVTVRALLH VWAGGPWPQG ATLRLDPTVL DAGELANRTG SVPRFRLLEG

PRHGRVVRVP RARTEPGGSQ LVEQFTQQDL EDGRLGLEVG RPEGRAPGPA GDSLTLELWA

QGVPPAVASL DFATEPYNAA RPYSVALLSV PEAARTEAGK PESSTPTGEP GPMASSPEPA

VAKGGFLSFL EANMFSVIIP MCLVLLLLAL ILPLLFYLRK RNKTGKHDVQ VLTAKPRNGL

AGDTETFRKV EPGQAIPLTA VPGQLFP
```

See also GENBANK® Accession No. AAI28111 incorporated herein by reference).

HMW-MAA is a human melanoma-associated chondroitin sulfate proteoglycan that plays a role in stabilizing cell-substratum interactions during early events of melanoma cell spreading on endothelial basement membranes. This molecule, also known as CSPG4, is an integral membrane chondroitin sulfate proteoglycan expressed by human malignant melanoma cells.

In vivo, it is present in a molecule that consists of two noncovalently associated glycopolypeptides. One has an apparent molecular weight of 280K, and the other has an apparent molecular weight greater than 440K. HMW-MAA is synthesized and expressed by human melanoma cells (Spiro, R. C. et al. F. Biol. Chem. 264:1779 (1989); Esko, J. D., et al., Science 241:1092, 1988). Proteoglycans are glycoproteins with glycosaminoglycan (GAG) polysaccharide chains covalently attached to the serine residue in their core. The HMW-MAA core protein is initially translated as a precursor with a molecular mass of 240K with asparagine N-linked oligosaccharides of the high mannose type.

In another example, the HMW-MAA is encoded by the nucleic acid sequence set forth as:

See also GENBANK® Accession No. BC128110, incorporated herein by reference. Once of skill in the art can readily use a nucleic acid sequence to produce a polypeptide, such as HMW-MAA using standard method in molecular biology (see, for example, *Molecular Cloning: A Laboratory Manual*, 2nd ed., vol. 1-3, ed. Sambrook et al., Cold Spring Harbor Laboratory Press, Cold Spring Harbor, N.Y., 1989).

The method disclosed herein can utilize monoclonal antibodies and antigen binding fragments thereof that specifically bind human HMW-MAA, including fully human monoclonal antibodies, chimeric antibodies and mouse monoclonal antibodies. In some embodiments, the human monoclonal antibody functional fragment is a scFv. Also described are compositions including the provided human monoclonal antibodies or functional fragment thereof and a pharmaceutically acceptable carrier. Nucleic acids encoding these antibodies, expression vectors comprising these nucleic acids, and isolated host cells that express the nucleic acids are also provided.

Antibodies that specifically bind HMW-MAA are disclosed, for example, in PCT Publication No. 2010/045495, incorporated herein by reference, which discloses a heavy (SEQ ID NO: 2)

```
gggagcagat gagggaggag ccagaggcag cataccgcct catccaggga ccccagtatg ggcatctcct ggtgggcggg cggcccacct cggccttcag ccaattccag atagaccagg gcgaggtggt ctttgccttc accaacttct cctcctctca tgaccacttc agagtcctgg cactggctag gggtgtcaat gcatcagccg tagtgaacgt cactgtgagg gctctgctgc atgtgtgggc aggtgggcca tggccccagg gtgccaccct gcgcctggac cccaccgtcc tagatgctgg cgagctggcc aaccgcacag gcagtgtgcc gcgcttccgc ctcctggagg gacccccggca tggccgcgtg gtccgcgtgc cccgagccag gacggagccc gggggcagcc agctggtgga gcagttcact cagcaggacc ttgaggacgg gaggctgggg ctggaggtgg gcaggccaga ggggagggcc cccggccccg caggtgacag tctcactctg gagctgtggg cacagggcgt cccgcctgct gtggcctccc tggactttgc cactgagcct tacaatgctg cccggcccta cagcgtggcc ctgctcagtg tccccgaggc cgcccggacg gaagcaggga agccagagag cagcaccccc acaggcgagc caggccccat ggcatccagc cctgagcccg ctgtggccaa gggaggcttc ctgagcttcc ttgaggccaa catgttcagc gtcatcatcc ccatgtgcct ggtacttctg ctcctggcgc tcatcctgcc cctgctcttc tacctccgaa aacgcaacaa gacgggcaag catgacgtcc aggtcctgac tgccaagccc cgcaacggcc tggctggtga caccgagacc tttcgcaagg tggagccagg ccaggccatc ccgctcacag ctgtgcctgg ccagttattt cca
``` chain. The following are heavy and light chain amino acid sequences of a human antibody (C21) that specifically binds HMW-MAA.

$V_H$
(SEQ ID NO: 3)
QVQLVQSGAEVKKPGSSVKVSCKASGGTFSSYAISWVRQAPGQGLE
WMGGIIPIFGTANYAQKFQGRVTITADESTSTAYMELSSLRSDDTA
VYYCARALDPITFDSWGQGTLVTVSR (118 amino acids)

$V_L$
(SEQ ID NO: 4)
SELTQDPAVSVALGQTVRITCQGDSLRSYYASWYQQKPGQAPVLVI
YGKNNRPSGIPDRFSGSSSGNTASLTITGAQAEDEADYYCNSRDSS
GNHVVFGGGTKLTVLGRS (110 amino acids)

For both $V_H$ (SEQ ID NO: 3) and $V_L$ (SEQ ID NO: 4), the location of the framework regions (FR) and CDRs is as follows:
FR1—amino acids 1-26
CDR1—amino acids 27-38
FR2—amino acids 39-55
CDR2—amino acids 56-65
FR3—amino acids 66-104
CDR3—amino acids 105-115 ($V_H$) or 105-110 ($V_L$)
In some examples, the heavy chain of the antibody comprises amino acids 27-38 of SEQ ID NO: 3 (CDR1), amino acids 56-65 of SEQ ID NO: 3 (CDR2), amino acids 105-115 of SEQ ID NO: 3 (CDR3), or a combination or subcombination thereof. In some examples, the light chain of the antibody comprises amino acids 27-38 of SEQ ID NO: 4 (CDR1), amino acids 56-65 of SEQ ID NO: 4 (CDR2), amino acids 105-110 of SEQ ID NO: 4 (CDR3), or a combination or subcombination thereof. The antibody can include a heavy chain comprising amino acids 27-38 of SEQ ID NO: 3 (CDR1), amino acids 56-65 of SEQ ID NO: 3 (CDR2), and amino acids 105-115 of SEQ ID NO: 3 (CDR3). The antibody can include a light chain comprising amino acids 27-38 of SEQ ID NO: 4 (CDR1), amino acids 56-65 of SEQ ID NO: 4 (CDR2), and amino acids 105-110 of SEQ ID NO: 4 (CDR3)

The monoclonal antibody of use in the methods disclosed herein can be a fully human antibody. Fully human monoclonal antibodies include human framework regions. The human framework regions can include the framework regions disclosed in one or both of SEQ ID NO: 3 or SEQ ID NO: 4 (these sequences include CDR sequences as well as framework sequences). However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16), which is herein incorporated by reference.

Additional antibodies of use that specifically bind HMW-MAA include mouse monoclonal antibodies 225.28 (see U.S. Pat. No. 5,126,262, incorporated herein by reference); 763.74 (see U.S. Pat. No. 5,493,009, incorporated herein by reference); VF1-TP41.2; VT80.112; 653.25; 763.74; TP61.5 and T8-203 (see PCT Publication No. 89/11296; Drake et al., Cancer Immunol. Immunother. DOI 10: 1007, s00262-008-0567-5, 2008; Goto et al., Clin. Cancer Res. 14: 3401-3407, 2008, all incorporated by reference herein). Monoclonal antibodies 225.28 and 763.74 were deposited previously by another at the American Type Culture Collection (ATCC, 10801 University Blvd., Manassas, Va. 20110). Hybridomas producing the monoclonal antibodies TP109.2 and VF20-VT1.7 were deposited at the American Type Culture Collection (ATCC) as ATCC Accession No. PTA-9582 and ATCC Accession No. PTA-9583, respectively, in accordance with the Budapest Treaty on Nov. 4, 2008. One of skill in the art can produced humanized forms of these antibodies.

In one embodiment, the antibody is monoclonal antibody (mAb) 225.28, or is a chimeric, humanized or fully human antibody that specifically binds the epitope bound by mAb 225.28. In a further embodiment, the antibody is an antigen binding fragment of monoclonal antibody (mAb) 225.28, a chimeric or humanized form of mAb 225.28. In other embodiments the antibody is a chimeric, humanized or fully human antibody that specifically binds the epitope bound by mAb 225.28. In other embodiments, the antibody is the monoclonal antibody TP109.2 or VF20-VT1.7. In a further embodiment, the antibody is an antigen binding fragment of monoclonal antibody TP109.2 or VF20-VT1.7. In additional embodiments, the antibody is a chimeric, humanized form of TP109.2 or VF20-VT1.7, or a chimeric, humanized or fully human antibody that specifically binds the epitope bound by TP109.2 or VF20-VT1.7.

In another specific example, the antibody is mAb 763.74, or is a chimeric, humanized or fully human antibody that specifically binds the epitope bound by mAb 763.74. Similarly, the antibody can be a functional fragment of mAb 763.74, or a functional fragment of a chimeric, humanized or fully human antibody that specifically binds the epitope bound by mAb 763.74. In some embodiments, the antibodies are any fully human antibody that specifically binds HMW-MAA.

Fully human monoclonal antibodies include human framework regions. The human framework regions can include the framework regions disclosed in one or both of SEQ ID NO: 3 or SEQ ID NO: 4 (these sequences include CDR sequences as well as framework sequences). However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16), which is herein incorporated by reference.

Chimeric antibodies include CDRs from one species, and framework regions (and/or a constant domain), from another species. In some embodiments, the monoclonal antibody, or antigen binding fragment, is chimeric. In one specific non-limiting example, the monoclonal antibody includes the CDRs from a murine antibody, and a human framework region. In another specific non-liming example, the monoclonal antibody includes the CDRs from a rabbit antibody, and a human framework region.

The monoclonal antibody of use in the disclosed methods can be of any isotype. The monoclonal antibody can be, for example, an IgA, IgM or an IgG antibody, such as $IgG_1$ or an $IgG_2$. The class of an antibody that specifically binds HMW-MAA can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds HMW-MAA that was originally IgM may be class switched to an IgG. Class switching can be used to convert one IgG subclass to another, such as from $IgG_1$ to $IgG_2$.

The method disclosed herein can utilize immunoconjugates comprising the monoclonal antibodies or functional fragment thereof that specifically binds human HMW-MAA, such as human monoclonal antibodies. The immunoconjugates can comprise any therapeutic agent, toxin or other moiety. In one example, the toxin is PE or a variant or fragment thereof.

Antibody fragments that specifically bind HMW-MAA are encompassed by the present disclosure, such as Fab, F(ab')$_2$, and Fv which include a heavy chain and light chain variable region and are capable of binding the epitopic determinant on HMW-MAA. These antibody fragments retain the ability to specifically bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of M912.

In a further group of embodiments, the antibodies are Fv antibodies, which are typically about 25 kDa and contain a complete antigen-binding site with three CDRs per each heavy chain and each light chain. To produce these antibodies, the V$_H$ and the V$_L$ can be expressed from two individual nucleic acid constructs in a host cell. If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise V$_H$ and V$_L$ chains connected by a peptide linker. These single-chain antigen binding proteins (scFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993; and Sandhu, supra). Dimers of a single chain antibody (scFV$_2$), are also contemplated.

The antibody can also be included in a bi-specific antibody. In further embodiments, an engineered antibody domain, including the heavy chain CDRs or the light chain CDRs can be utilized, provided the engineered antibody domain specifically binds HMW-MAA (CSPG4).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the V$_H$ and the V$_L$ regions to increase yield. Conservative amino acid substitution tables providing functionally similar amino acids are well known to one of ordinary skill in the art.

In some embodiments, the disclosed methods utilize immunoconjugates. Immunoconjugates include, but are not limited to, molecules in which there is a covalent linkage of a diagnostic or therapeutic agent with an antibody. A therapeutic agent is an agent with a particular biological activity directed against a particular target molecule or a cell bearing a target molecule. Therapeutic agents include various drugs such as vinblastine, daunomycin and the like, and effector molecules such as cytotoxins such as native or modified *Pseudomonas* exotoxin or Diphtheria toxin, encapsulating agents (e.g., liposomes), which themselves contain pharmacological compositions, target moieties and ligands.

The choice of a particular therapeutic agent depends on the particular target molecule or cell and the biological effect desired. Thus, for example, the therapeutic agent may be an effector molecule that is cytotoxin which is used to bring about the death of a particular target cell. Conversely, where it is merely desired to invoke a non-lethal biological response, a therapeutic agent can be conjugated to a non-lethal pharmacological agent or a liposome containing a non-lethal pharmacological agent.

Toxins can be employed with antibodies that bind HMW-MAA polypeptide and antigen biding antibody fragments, such as a svFv or a dsFv, to yield chimeric molecules, which are of use as immunotoxins. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.).

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, *J. Virol.* 19:220, 1976), and has been used in human clinical trials. See, U.S. Pat. Nos. 5,792,458 and 5,208,021. As used herein, the term "diphtheria toxin" refers as appropriate to native diphtheria toxin or to diphtheria toxin that retains enzymatic activity but which has been modified to reduce non-specific toxicity.

Ricin is the lectin RCA60 from *Ricinus communis* (Castor bean). The term "ricin" also references toxic variants thereof. For example, see U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Ribonucleases have also been conjugated to targeting molecules for use as immunotoxins (see Suzuki et al., *Nat Biotech* 17:265-270, 1999). Exemplary ribotoxins such as α-sarcin and restrictocin are discussed in, e.g., Rathore et al., *Gene* 190:31-35, 1997; and Goyal and Batra, *Biochem* 345 Pt 2:247-254, 2000. Calicheamicins were first isolated from *Micromonospora echinospora* and are members of the enediyne antitumor antibiotic family that cause double strand breaks in DNA that lead to apoptosis (see, e.g., Lee et al., *J. Antibiot* 42:1070-1087. 1989). The drug is the toxic moiety of an immunotoxin in clinical trials (see, e.g., Gillespie et al., *Ann Oncol* 11:735-741, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu et al., *Agr. Biol. Chem.* 52:1095, 1988; and Olsnes, *Methods Enzymol.* 50:330-335, 1978).

In one embodiment, the toxin is *Pseudomonas* exotoxin (PE). Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence and the sequence of modified PE are provided in U.S. Pat. No. 5,602,095, incorporated herein by reference. In one embodiment, native PE has a sequence set forth as:

```
                                          (SEQ ID NO: 5)
AEEAFDLWNE CAKACVLDLK DGVRSSRMSV DPAIADTNGQ

GVLHYSMVLE GGNDALKLAI DNALSITSDG LTIRLEGGVE

PNKPVRYSYT RQARGSWSLN WLVPIGHEKP SNIKVFIHEL

-continued
NAGNQLSHMS PIYTIEMGDE LLAKLARDAT FFVRAHESNE

MQPTLAISHA GVSVVMAQTQ PRREKRWSEW ASGKVLCLLD

PLDGVYNYLA QQRCNLDDTW EGKIYRVLAG NPAKHDLDIK

PTVISHRLHF PEGGSLAALT AHQACHLPLE TFTRHRQPRG

WEQLEQCGYP VQRLVALYLAARLSWNQVDQ VIRNALASPG

SGGDLGEAIR EQPEQARLAL TLAAAESERF VRQGTGNDEA

GAANADVVSL TCPVAAGECA GPADSGDALL ERNYPTGAEF

LGDGGDVSFS TRGTQNWTVE RLLQAHRQLE ERGYVFVGYH

GTFLEAAQSI VFGGVRARSQ DLDAIWRGFY IAGDPALAYG

YAQDQEPDAR GRIRNGALLR VYVPRSSLPG FYRTSLTLAA

PEAAGEVERL IGHPLPLRLD AITGPEEEGG RLETILGWPL

AERTVVIPSA IPTDPRNVGG DLDPSSIPDK

EQAISALPDYASQPGKPPRE DLK
```

The method of action of PE is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall et al., *J. Biol. Chem.* 264:14256-14261, 1989.

The term "*Pseudomonas* exotoxin" ("PE") as used herein refers as appropriate to a full-length native (naturally occurring) PE or to a PE that has been modified. Such modifications may include, but are not limited to, elimination of domain Ia, various amino acid deletions in domains Ib, II and III, single amino acid substitutions and the addition of one or more sequences at the carboxyl terminus, such as KDEL (SEQ ID NO: 6) and REDL (SEQ ID NO: 7) (see Siegall et al., supra). In several examples, the cytotoxic fragment of PE retains at least 50%, such as about 75%, about 90%, or about 95% of the cytotoxicity of native PE. In one embodiment, the cytotoxic fragment is more toxic than native PE.

Thus, the PE used in the immunotoxins disclosed herein includes the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE known in the art include PE40, PE38, and PE35.

In several embodiments, the PE has been modified to reduce or eliminate non-specific cell binding, typically by deleting domain Ia, as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E") exhibits greatly diminished non-specific cytotoxicity. This mutant form of PE is sometimes referred to as PE4E.

PE40 is a truncated derivative of PE (see, Pai et al., *Proc. Nat'l Acad. Sci. U.S.A.* 88:3358-3362, 1991; and Kondo et al., *J. Biol. Chem.* 263:9470-9475, 1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827.

In some embodiments, the cytotoxic fragment PE38 is employed. PE38 is a truncated PE pro-protein composed of amino acids 253-364 and 381-613 of SEQ ID NO: 3 which is activated to its cytotoxic form upon processing within a cell (see e.g., U.S. Pat. No. 5,608,039, and Pastan et al., *Biochim. Biophys. Acta* 1333:C1-C6, 1997).

While in some embodiments, the PE is PE4E, PE40, or PE38, any form of PE in which non-specific cytotoxicity has been eliminated or reduced to levels in which significant toxicity to non-targeted cells does not occur can be used in the immunotoxins disclosed herein so long as it remains capable of translocation and EF-2 ribosylation in a targeted cell.

Conservatively modified variants of PE or cytotoxic fragments thereof have at least about 80% sequence identity, such as at least about 85% sequence similarity, at least about 90% sequence identity, or at least about 95% sequence similarity at the amino acid level, with the PE of interest, such as PE38.

With the antibodies and immunotoxins herein provided, one of skill can readily construct a variety of clones containing functionally equivalent nucleic acids, such as nucleic acids which differ in sequence but which encode the same effector molecule ("EM") or antibody sequence. Thus, nucleic acids encoding antibodies and conjugates and fusion proteins are provided herein.

Nucleic Acids

Nucleic acids encoding antibodies that specifically bind HMW-MAA, and conjugates and fusion thereof, are provided herein. These nucleic acids can be used in conjunction with a BRAF inhibitor. With the antibodies and immunotoxins herein provided, one of skill can readily construct a variety of clones containing functionally equivalent antibodies, and nucleic acids encoding these antibodies, such as nucleic acids which differ in sequence but which encode the same effector molecule ("EM") or antibody sequence. Thus, nucleic acids encoding antibodies and conjugates and fusion proteins are provided herein.

Nucleic acid sequences encoding the antibodies and/or immunotoxins can be prepared by any suitable method including, for example, cloning of appropriate sequences or by direct chemical synthesis by methods such as the phosphotriester method of Narang, et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, e.g., using an automated synthesizer as described in, for example, Needham-VanDevanter et al. *Nucl. Acids Res.* 12:6159-6168, 1984; and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In one embodiment, the nucleic acid sequences encoding the antibody or immunotoxin are prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill In one example, an immunotoxin of use is prepared by inserting the cDNA which encodes a variable region into a vector which comprises the cDNA encoding the EM. The insertion is made so that the variable region and the EM are read in frame so that one continuous polypeptide is produced. The polypeptide contains a functional Fv region and a functional EM region. In one embodiment, cDNA encoding a cytotoxin is ligated to a scFv so that the cytotoxin is located at the carboxyl terminus of the scFv. In one example, cDNA encoding a *Pseudomonas* exotoxin ("PE"), mutated to eliminate or to reduce non-specific binding, is ligated to a scFv so that the toxin is located at the amino terminus of the scFv. In another example, PE38 is located at the amino terminus of the scFv. In a further example, cDNA encoding a cytotoxin is ligated to a heavy chain variable region of an antibody that binds the antigen of interest so that the cytoxin is located at the carboxyl terminus of the heavy chain variable region. The heavy chain-variable region can subsequently be ligated to a light chain variable region of the antibody using disulfide bonds. In yet another example, cDNA encoding a cytotoxin is ligated to a light chain variable region of an antibody that binds the antigen (for example, HMW-MAA), so that the cytotoxin is located at the carboxyl terminus of the light chain variable region. The light chain-variable region can subsequently be ligated to a heavy chain variable region of the antibody using disulfide bonds.

Once the nucleic acids encoding the antibody immunotoxin is isolated and cloned, the protein can be expressed in a recombinantly engineered cell such as bacteria, plant, yeast, insect and mammalian cells. One or more DNA sequences encoding an antibody immunotoxin can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the antibody or immunotoxin can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody or immunotoxin can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the immunotoxin, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide may be carried out by conventional means including preparative chromatography and immunological separations. Once expressed, the recombinant immunotoxins can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (e.g., 100-fold) of the denatured and reduced protein into refolding buffer. An exemplary buffer is 0.1 M Tris, pH 8.0, 0.5 M 1-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. It is desirable to add excess oxidized glutathione or other oxidizing low molecular weight compounds to the refolding solution after the redox-shuffling is completed.

In addition to recombinant methods, the immunoconjugates, EM, and antibodies disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are well known in the art.

BRAF Inhibitors

The methods disclosed herein utilize BRAF inhibitors. One exemplary amino acid sequence for human BRAF is provided below.

```
         (SEQ ID NO:10, see GENBANK ® Accession No.
       ACD11489.1, incorporated herein by reference)
    MAALSGGGGG GAEPGQALFN GDMEPEAGAG AGAAASSAAD

PAIPEEVWNI KQMIKLTQEHIEALLDKFGG EHNPPSIYLE

AYEEYTSKLD ALQQREQQLL ESLGNGTDFS

VSSSASMDTVTSSSSSSLSV LPSSLSVFQN PTDVARSNPK

SPQKPIVRVF LPNKQRTVVP ARCGVTVRDSLKKALMMRGL

IPECCAVYRI QDGEKKPIGW DTDISWLTGE ELHVEVLENV

PLTTHNFVRKTFFTLAFCDF CRKLLFQGFR CQTCGYKFHQ

RCSTEVPLMC VNYDQLDLLF VSKFFEHHPIPQEEASLAET

ALTSGSSPSA PASDSIGPQI LTSPSPSKSI PIPQPFRPAD

EDHRNQFGQRDRSSSAPNVH INTIEPVNID DLIRDQGFRG
```

-continued

```
DGGSTTGLSA TPPASLPGSL TNVKALQKSPGPQRERKSSS

SSEDRNRMKT LGRRDSSDDW EIPDGQITVG QRIGSGSFGT

VYKGKWHGDVAVKMLNVTAP TPQQLQAFKN EVGVLRKTRH

VNILLFMGYS TKPQLAIVTQ WCEGSSLYHHLHIIETKFEM

IKLIDIARQT AQGMDYLHAK SIIHRDLKSN NIFLHEDLTV

KIGDFGLATV KSRWSGSHQF EQLSGSILWM APEVIRMQDK

NPYSFQSDVY AFGIVLYELM TGQLPYSNINNRDQIIFMVG

RGYLSPDLSK VRSNCPKAMK RLMAECLKKK RDERPLFPQI

LASIELLARSLPKIHRSASE PSLNRAGFQT EDFSLYACAS

PKTPIQAGGY GAFPVH
```

A number of BRAF inhibitors have been previously described (see, for example, PCT Publication Nos. WO 2007/002325, WO 2007/002433, WO 2009/047505, WO 03/086467; WO 2009/143024, WO 2010/104945, WO 2010/104973, WO 2010/111527 and WO 2009/152087; U.S. Pat. Nos. 6,187,799 and 7,329,670; and U.S. Patent Application Publication Nos. 2005/0176740 and 2009/0286783, each of which is herein incorporated by reference).

PLX 4032 (also known as RG7204, RO5185426, and Vemurafenib, $C_{23}H_{18}ClF_2N_3O_3S$) is a BRAF small molecule inhibitor being developed by Plexxikon and Roche (Genentech) for the treatment of melanoma. Phase I clinical trials in patients with advanced melanoma demonstrated that PLX 4032 was effective in promoting tumor regression and increasing overall survival in patients with the V600E BRAF mutation. In particular embodiments of the present disclosure, the BRAF inhibitor is PLX 4032:

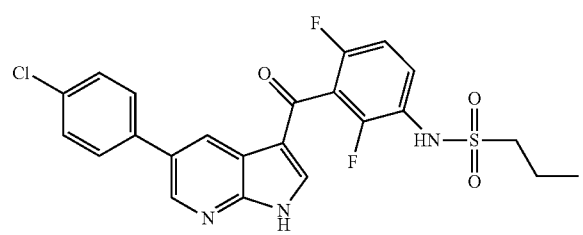 [SMILES: CCCS(=O)(=O)Nc1ccc(F)c(C(=O)c2c[nH]c3ncc(-c4ccc(Cl)cc4)cc23)c1F]

or a salt, solvate or functional derivative thereof. Thus, a therapeutically effective amount of PLX4032 can be used in combination with a therapeutically effective amount of an antibody that specifically binds HMW-MAA (or a nucleic acid encoding this antibody) for the treatment of tumors.

In other embodiments, the BRAF inhibitor is PLX 4720 ($C_{17}H_{14}ClF_2N_3O_3S$):

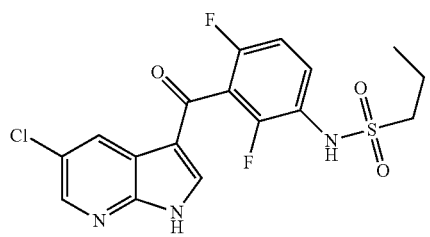 [SMILES: CCCS(=O)(=O)Nc1ccc(F)c(C(=O)c2c[nH]c3ncc(Cl)cc23)c1F]

or a salt, solvate or functional derivative thereof. Thus, a therapeutically effective amount of PLX4720 can be used in combination with a therapeutically effective amount of an antibody that specifically binds HMW-MAA (or a nucleic acid encoding this antibody) for the treatment of tumors.

In further embodiments, the BRAF inhibitor is sofafenib ($C_{21}H_{16}ClF_3N_4O_3$):

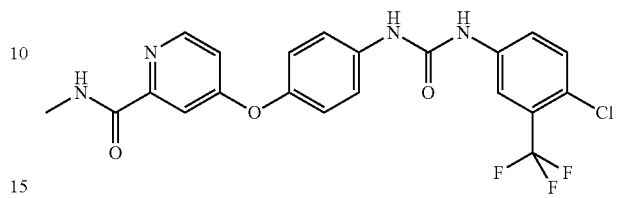

or a salt, solvate or functional derivative thereof. Sofafenib (Nexavar) is used for the treatment of renal cancer, liver cancer, thyroid cancer, lung cancer, glioblastoma and kidney cancer. Thus a therapeutically effective amount of sofafenib can be used in combination with a therapeutically effective amount of an antibody that specifically binds HMW-MAA (or a nucleic acid encoding this antibody) for the treatment of these tumors.

In some embodiments, the BRAF inhibitors have the structure of Formula III, shown below, or any salts, prodrugs, tautomers or isomers thereof, as described in PCT Publication Nos. WO 2007/002325 and WO 2007/002433 (which are incorporated herein by reference):

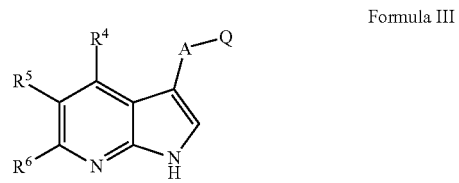

Formula III wherein: Q has a structure selected from the group consisting of

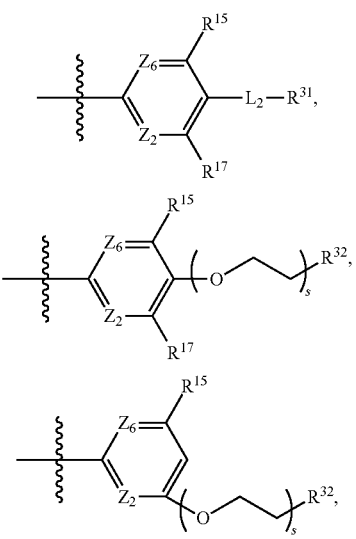

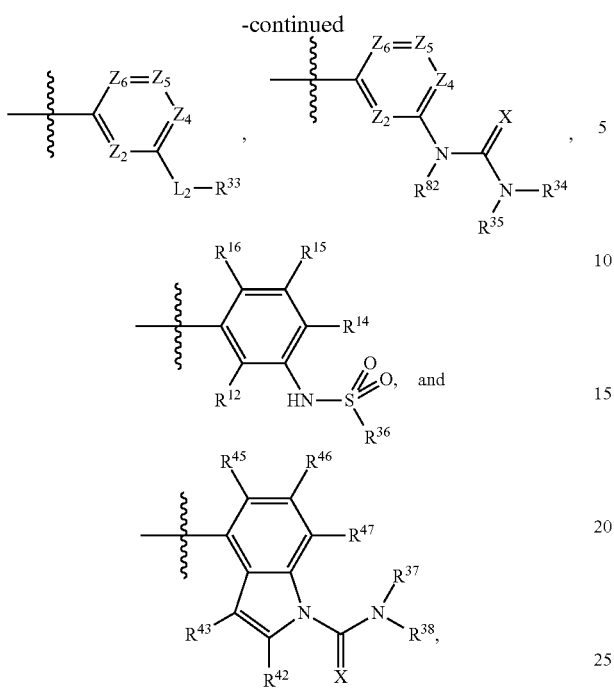

in which $\xi$ indicates the attachment point of Q to A of Formula III;

$Z_2$ is N or $CR^{12}$; $Z_4$ is N or $CR^{14}$; $Z_5$ is N or $CR^{15}$; $Z_6$ is N or $CR^{16}$;

$L_2$ is selected from the group consisting of $-(CR^{10}R^{11})_p-NR^{25}-(CR^{10}R^{11})_q-$, $-(CR^{10}R^{11})_p-O-(CR^{10}R^{11})_q-$, $-(CR^{10}R^{11})_p-S-(CR^{10}R^{11})_q-$, $-(CR^{10}R^{11})_p-C(O)-(CR^{10}R^{11})_q-$, $-(CR^{10}R^{11})_p-C(S)-(CR^{10}R^{11})_q-$, $-(CR^{10}R^{11})_p-S(O)-(CR^{10}R^{11})_q-$, $-(CR^{10}R^{11})_p-S(O)_2-(CR^{10}R^{11})_q-$, $-(CR^{10}R^{11})_p-C(O)NR^{25}-(CR^{10}R^{11})_q-$, $-(CR^{10}R^{11})_p-C(S)NR^{25}-(CR^{10}R^{11})_q-$, $-(CR^{10}R^{11})_p-S(O)_2NR^{25}-(CR^{10}R^{11})_q-$, $-(CR^{10}R^{11})_p-NR^{25}C(O)-(CR^{10}R^{11})_q-$, $-(CR^{10}R^{11})_p-NR^{25}C(S)-(CR^{10}R^{11})_q-$, and $-(CR^{10}R^{11})_p-NR^{25}S(O)_2-(CR^{10}R^{11})_q-$;

p and q are independently 0, 1, or 2 provided, however, that at least one of p and q is 0;

s is 1 or 2;

X is O or S;

A is selected from the group consisting of $-O-$, $-S-$, $-CR^aR^b-$, $-C(O)-$, $-C(S)-$, $-S(O)-$, and $-S(O)_2-$;

$R^a$ and $R^b$ at each occurrence are independently selected from the group consisting of hydrogen, fluoro, $-OH$, $-NH_2$, lower alkyl, lower alkoxy, lower alkylthio, mono-alkylamino, di-alkylamino, and $-NR^3R^9$, wherein the alkyl chain(s) of lower alkyl, lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or $R^a$ and $R^b$ combine to form a 3-7 membered monocyclic cycloalkyl or 5-7 membered monocyclic heterocloalkyl, wherein the monocyclic cycloalkyl or monocyclic heterocycloalkyl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^1$ is selected from the group consisting of hydrogen, lower alkyl, cycloalkyl, heterocycloalkyl, aryl, heteroaryl, $-C(O)R^7$, $-C(S)R^7$, $-S(O)_2R^7$, $-C(O)NHR^7$, $-C(S)NHR^7$, and $-S(O)_2NHR^7$, wherein lower alkyl is optionally substituted with one or more substituents selected from the group consisting of fluoro, $-OH$, $-NH_2$, lower alkoxy, lower alkylthio, mono-alkylamino, di-alkylamino, and $-NR^8R^9$, wherein the alkyl chain(s) of lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, further provided that when $R^1$ is lower alkyl, any substitution on the lower alkyl carbon bound to the N of $-NR^1-$ is fluoro, and wherein cycloalkyl, heterocloalkyl, aryl or heteroaryl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^7$ is selected from the group consisting of lower alkyl, cycloalkyl, heterocycloalkyl, aryl, and heteroaryl, wherein lower alkyl is optionally substituted with one or more substituents selected from the group consisting of fluoro, $-OH$, $-NH_2$, lower alkoxy, lower alkylthio, mono-alkylamino, di-alkylamino, and $-NR^8R^9$, provided, however, that any substitution of the alkyl carbon bound to the N of $-C(O)NHR^7$, $-C(S)NHR^7$ or $-S(O)_2NHR^7$ is fluoro, wherein the alkyl chain(s) of lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein cycloalkyl, heterocycloalkyl, aryl and heteroaryl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^4$, $R^5$, $R^6$, $R^{12}$, $R^{14}$, $R^{15}$, $R^{16}$, $R^{42}$, $R^{43}$, $R^{45}$, $R^{46}$ and $R^{47}$ are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, and —LR$^{26}$;

L at each occurrence is independently selected from the group consisting of -(alk)$_a$-S-(alk)$_b$-, -(alk)$_a$-O-(alk)$_b$-, -(alk)$_a$-NR$^{25}$-(alk)$_b$-, -(alk)$_a$-C(O) -(alk)$_b$-, -(alk)$_a$-C(S)-(alk)$_b$-, -(alk)$_a$-S(O)-(alk)$_b$-, -(alk)$_a$-S(O)$_2$-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)NR$^{25}$-(alk)$_b$-, -(alk)$_a$-C(S)NR$^{25}$-(alk)$_b$-, -(alk)$_a$-S(O)$_2$NR$^{25}$-(alk)$_b$-, -(alk)$_a$-NR$^{25}$C(O)-(alk)$_b$-, -(alk)$_a$-NR$^{25}$C(S)-(alk)$_b$-, -(alk)$_a$-NR$^{25}$S(O)$_2$-(alk)$_b$-, -(alk)$_a$-NR$^{25}$C(O)O-(alk)$_b$-, -(alk)$_a$-NR$^{25}$C(S)O-(alk)$_b$-, -(alk)$_a$-OC(O)NR$^{25}$-(alk)$_b$-, -(alk)$_a$-OC(S)NR$^{25}$-(alk)$_b$-, -(alk)$_a$-NR$^{25}$C(O)NR$^{25}$-(alk)$_b$-, -(alk)$_a$-NR$^{25}$C(S)NR$^{25}$-(alk)$_b$-, and -(alk)$_a$-NR$^{25}$S(O)$_2$NR$^{25}$-(alk)$_b$-;

a and b are independently 0 or 1;

alk is C$_{1-3}$ alkylene or C$_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^8$R$^9$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

R$^{25}$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl;

R$^{26}$ at each occurrence is independently selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when R$^{26}$ is optionally substituted lower alkenyl, no alkene carbon thereof is bound to N, S, O, S(O), S(O)$_2$, C(O) or C(S) of L, optionally substituted lower alkynyl, provided, however, that when R$^{26}$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl;

R$^{10}$ and R$^{11}$ at each occurrence are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino; or any two of R$^{10}$ and R$^{11}$ on the same or adjacent carbon atoms combine to form a 3-7 membered monocyclic cycloalkyl or 5-7 membered monocyclic heterocycloalkyl, and any others of R$^{10}$ and R$^{11}$ are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R$^8$ and R$^9$ combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

R$^{17}$ is selected from the group consisting of hydrogen, halogen, optionally substituted lower alkyl and —OR$^{18}$;

R$^{31}$ and R$^{33}$ are independently selected from the group consisting of optionally substituted aryl, optionally substituted heteroaryl, optionally substituted cycloalkyl, and optionally substituted heterocycloalkyl;

R$^{36}$ is selected from the group consisting of substituted methyl, optionally substituted C$_{2-6}$ alkyl, optionally substituted lower alkenyl, provided, however, that when R$^{36}$ is optionally substituted lower alkenyl, no alkene carbon thereof is bound to the S(O)$_2$ of S(O)$_2$R$^{36}$, optionally substituted lower alkynyl, provided, however, that when R$^{36}$ is optionally substituted lower alkynyl, no alkyne carbon thereof is bound to the S(O)$_2$ of S(O)$_2$R$^{36}$, optionally substituted cycloalkyl, optionally substituted heterocycloalkyl, optionally substituted aryl, optionally substituted heteroaryl, and —NR$^{19}$R$^{20}$;

R$^{19}$, R$^{20}$, R$^{34}$, R$^{35}$, R$^{37}$, and R$^{38}$ are independently selected from the group consisting of hydrogen, optionally substituted lower alkyl, optionally substituted lower alkenyl, provided, however, that when R$^{19}$, R$^{20}$, R$^{34}$, R$^{35}$, R$^{37}$, or R$^{38}$ is optionally substituted lower alkenyl, no alkene carbon thereof is bound to the N of NR$^{19}$R$^{20}$, NR$^{34}$R$^{35}$ or NR$^{37}$R$^{38}$, optionally substituted lower alkynyl, provided, however, that when R$^{19}$, R$^{20}$, R$^{34}$, R$^{35}$, R$^{37}$, or R$^{38}$ is optionally substituted lower alkynyl, no alkyne carbon thereof is bound to the N of NR$^{19}$R$^{20}$, NR$^{34}$R$^{35}$ or NR$^{37}$R$^{38}$, optionally substituted cycloalkyl, optionally substituted heterocycloalkyl, optionally substituted aryl and optionally substituted heteroaryl; or R$^{34}$ and R$^{35}$ together with the nitrogen to which they are attached form optionally substituted 5-7 membered heterocycloalkyl or optionally substituted 5 or 7 membered nitrogen containing heteroaryl; or R$^{37}$ and R$^{38}$ together with the nitrogen to which they are attached form optionally substituted 5-7 membered heterocycloalkyl or optionally substituted 5 or 7 membered nitrogen containing heteroaryl;

R$^{32}$ is selected from the group consisting of hydrogen, optionally substituted lower alkyl, optionally substituted cycloalkyl, optionally substituted heterocycloalkyl, optionally substituted aryl, optionally substituted heteroaryl, and —OR$^{18}$;

R$^{82}$ is selected from hydrogen or lower alkyl; and

R$^{18}$ is hydrogen or optionally substituted lower alkyl;

In other embodiments of the present disclosure, the BRAF inhibitor comprises a formula as described in PCT Publication No. WO 03/086467 (incorporated herein by reference) as Formula I, Formula II or Formula III:

Formula I-

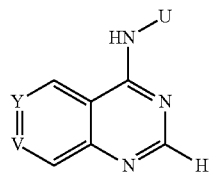

or a salt, solvate, physiologically functional derivative thereof;
wherein
Y is $CR^1$ and V is N;
or Y is $CR^1$ and V is $CR^2$;
$R^1$ represents a group $CH_3SO_2CH_2CH_2NHCH_2$—Ar—, wherein Ar is selected from phenyl, furan, thiophene, pyrrole and thiazole, each of which may optionally be substituted by one or two halo, $C_{1-4}$ alkyl or $C_{1-4}$ alkoxy groups;
$R^2$ is selected from the group comprising hydrogen, halo, hydroxy, $C_{1-4}$ alkyl, $C_{1-4}$ alkoxy, $C_{1-14}$ alkylamino and di[$C_{1-4\ alkyl}$]amino;
U represents a phenyl, pyridyl, 3H-imidazolyl, indolyl, isoindolyl, indolinyl, isoindolinyl, 1H-indazolyl, 2,3-dihydro-1H-indazolyl, 1H-benzimidazolyl, 2,3-dihydro-1H-benzimidazolyl or 1H-benzotriazolyl group, substituted by an $R^3$ group and optionally substituted by at least one independently selected $R^4$ group;

$R^3$ is selected from a group comprising benzyl, halo-, dihalo- and trihalobenzyl, benzoyl, pyridylmethyl, pyridylmethoxy, phenoxy, benzyloxy, halo-, dihalo- and trihalobenzyloxy and benzenesulphonyl;
or $R^3$ represents trihalomethylbenzyl or trihalomethylbenzyloxy;
or $R^3$ represents a group of formula

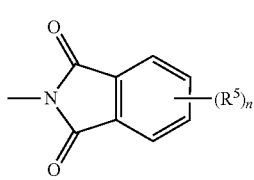

wherein each $R^5$ is independently selected from halogen, $C_{1-4}$ alkyl and $C_{1-14}$ alkoxy; and n is 0 to 3;

each $R^4$ is independently hydroxy, halogen, $C_{1-4}$ alkyl, $C_{2-4}$ alkenyl, $C_{2-4}$ alkynyl, $C_{1-4}$ alkoxy, amino, $C_{1-4}$ alkylamino, di[$C_{1-4}$ alkyl]amino, $C_{1-4}$ alkylthio, $C_{1-4}$ alkylsulphinyl, $C_{1-4}$ alkylsulphonyl, $C_{1-4}$ alkylcarbonyl, carboxy, carbamoyl, $C_{1-4}$ alkoxycarbonyl, $C_{1-4}$ alkanoylamino, N—($C_{1-4}$alkyl)carbamoyl, N,N-di ($C_{1-4}$ alkyl) carbamoyl, cyano, nitro and trifluoromethyl.

Additional BRAF inhibitors are shown below:

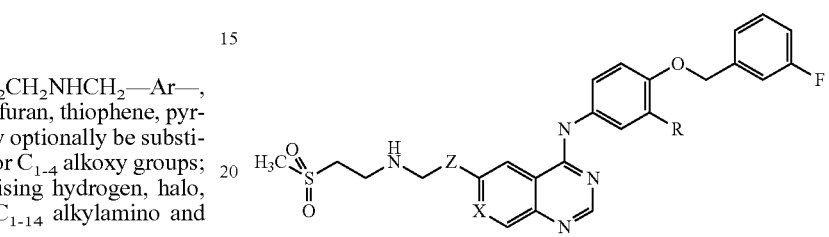

wherein R is —Cl or —Br, X is CH, N, or CF, and Z is thiazole or furan.

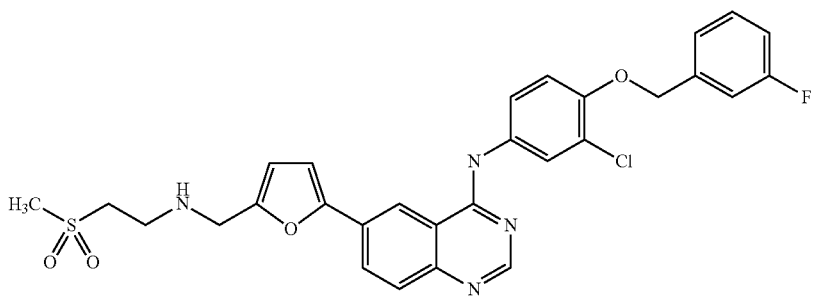 [SMILES: CS(=O)(=O)CCNCc1ccc(-c2ccc3ncnc(Nc4ccc(OCc5cccc(F)c5)c(Cl)c4)c3c2)o1]

In some embodiments, the BRAF inhibitor is selected from a compound as described in PCT Publication No. WO 2010/104973 which is incorporated by reference herein. These include the following:
In a first aspect, a compound selected from the group consisting of N-[3-(4-cyano-1H-pyrrolo[2,3-b]pyridine-3-carbonyl)-2,4-difluoro-phenyl]-4-trifluorometh/1-benzenesulfonamide (P-0001), N-[3-(4-ethynyl-1H-pyrrolo[2,3-b]pyridine-3-carbonyl)-2,4-difluoro-phenyl]-4-trifluoromethyl-benzenesulfonamide (P-0002), any salt thereof, any formulation thereof, any conjugate thereof, any derivative thereof, and any form thereof is provided. In certain embodiments P-0001, P-0002, or a salt thereof, formulation thereof, conjugate thereof, derivative thereof, or form thereof is an inhibitor of one or more Raf protein kinases, including A-Raf, B-Raf, and c-Raf-1 (including any mutations of these kinases),
In a second aspect the compound N-[3-(4-cyano-1H-pyrrolo[2,3-b]pyridine-3-carbonyl)-2,4-difluoro-phenyl]-4-trifluoromethyl-benzenesulfonamide (P-0001), or a salt thereof, formulation thereof, conjugate thereof, derivative thereof, or form thereof is provided. In certain embodiments P-0001, or a salt thereof, formulation thereof, conjugate thereof, derivative thereof, or form thereof is an inhibitor of one or mnre Raf protein kinases, including A-Raf, B-Raf, and c-Raf-1 (including any mutations of these kinases).

In a third aspect the compound N-[3-(4-ethynyl-1H-pyrrolo[2,3-b]pyridine-3-carbonyl)-2,4-difluoro-phenyl]-4-trifluoromethyl-benzenesulfonamide (P-0002), or a salt thereof, formulation thereof, conjugate thereof, derivative thereof, or form thereof is provided. In certain embodiments P-0002, or a salt thereof, formulation thereof, conjugate thereof, derivative thereof, or form thereof is an inhibitor of one or more Raf protein kinases, including A-Raf, B-Raf, and c-Raf-1 (including any mutations of these kinases).

In some embodiments, the BRAF inhibitor is selected from a compound as described in PCT Publication No. WO 2010/104945, which is incorporated by reference herein. These include the following:

In a first aspect, a compound selected from the group consisting of propane-1-sulfonic acid {2,4-difluoro-3-[5-(2-methoxy-pyrimidin-5-yl)-1H-pyr[tau]olo[2,3-b]pyridine-3-carbonyl]-phenyl}-amide (P-0001), propane-1-sulfonic acid [3-(5-cyano-1H-pyrrolo[2,3-b]pyridine-3-carbonyl)-2,4-difluoro-phenyl]-amide (P-0002), propane-1-sulfonic acid [3-(5-cyano-1H-pyrrolo[2,3-b]pyridine-3-carbonyl)-2-fluoro-phenyl]-amide (P-0003), N-[3-(5-cyano-1H-pyrrolo[2,3-b]pyridine-3-carbonyl)-2,4-difluoro-phenyl]-2,5-diflu[upsilon]r[upsilon]-ben/enesulfonamide (P-0004), N-[3-(5-cyano-1H-pyrrolo[2,3-b]pyridine-3-carbonyl)-2,4-difluoro-phenyl]-3-fluoro-benzenesulfonamide (P-0005), pyrrolidine-1-sulfonic acid [3-(5-cyano-1H-pyi[tau]olo[2,3-b]pyridine-3-carbonyl)-2,4-difluoro-phenyl]-amide (P-0006), N,N-dimethylamino-sulfonic acid [3-(5-cyano-1H-pyrrolo[2,3-b]pyridine-3-carbonyl)-2.4-difluoro-phenyl]-amide (P-0007). any salt thereof, any formulation thereof, any conjugate thereof, any derivative thereof, and any form thereof is provided. In certain embodiments P-0001, P-0002, P-0003, P-0004, P-0005, P-0006, P-0007. or a salt thereof, formulation thereof, conjugate thereof, derivative thereof, or form thereof is an inhibitor of one or more Raf prolei[pi]kinases, including [Lambda]-Raf, R-Raf. and c-Raf-1 (including any mutations of these kinases).

In some embodiments, the BRAF inhibitor is a compound having a formula from U.S. Pat. No. 6,187,799, which is incorporated by reference herein:

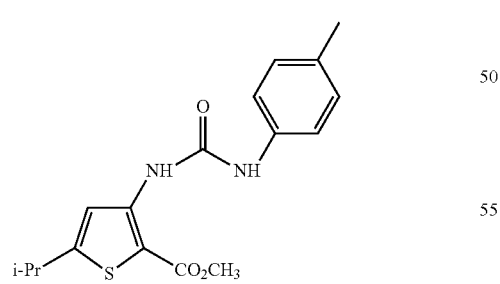

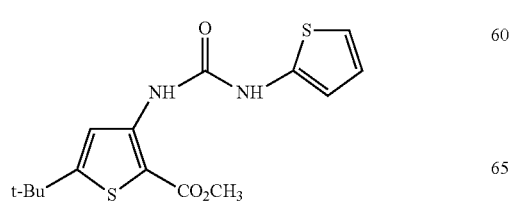

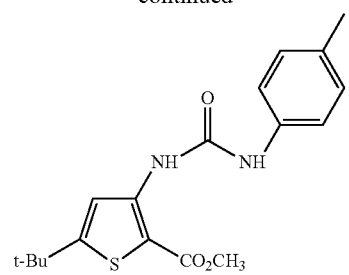

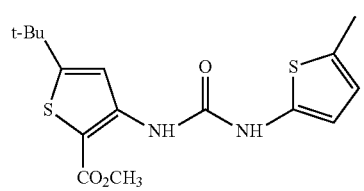

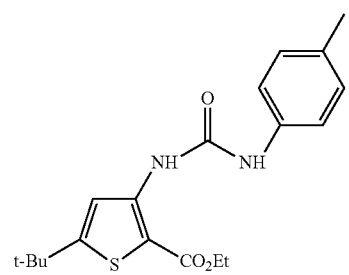

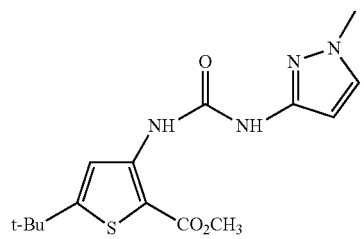

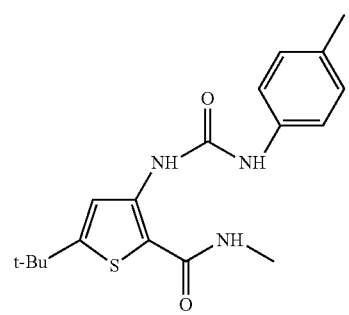

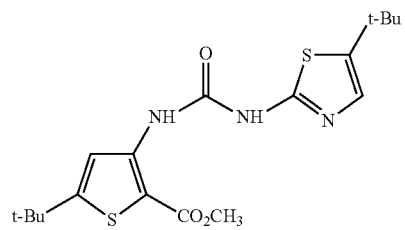

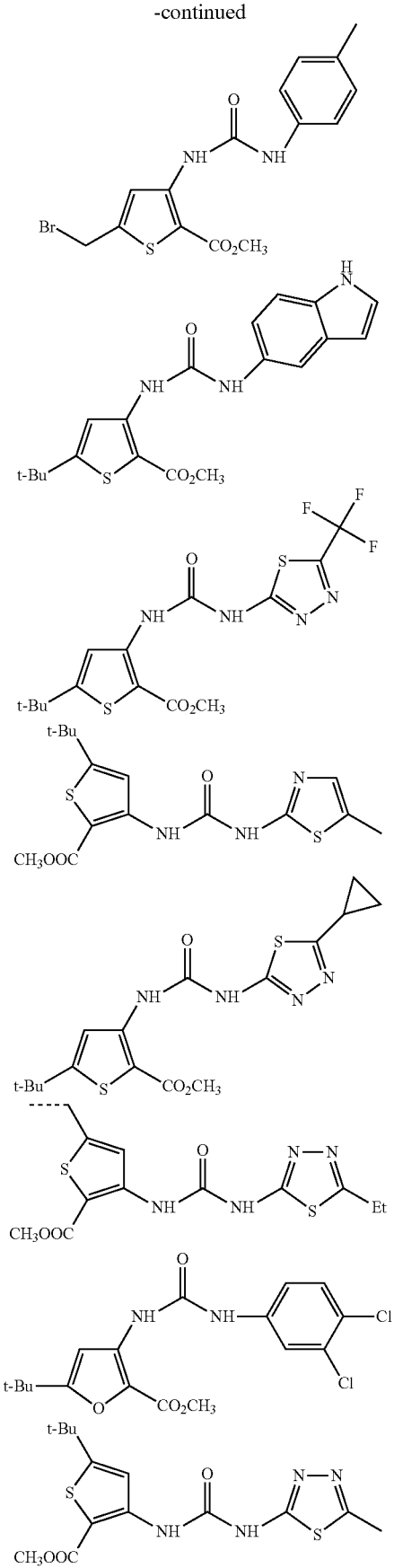
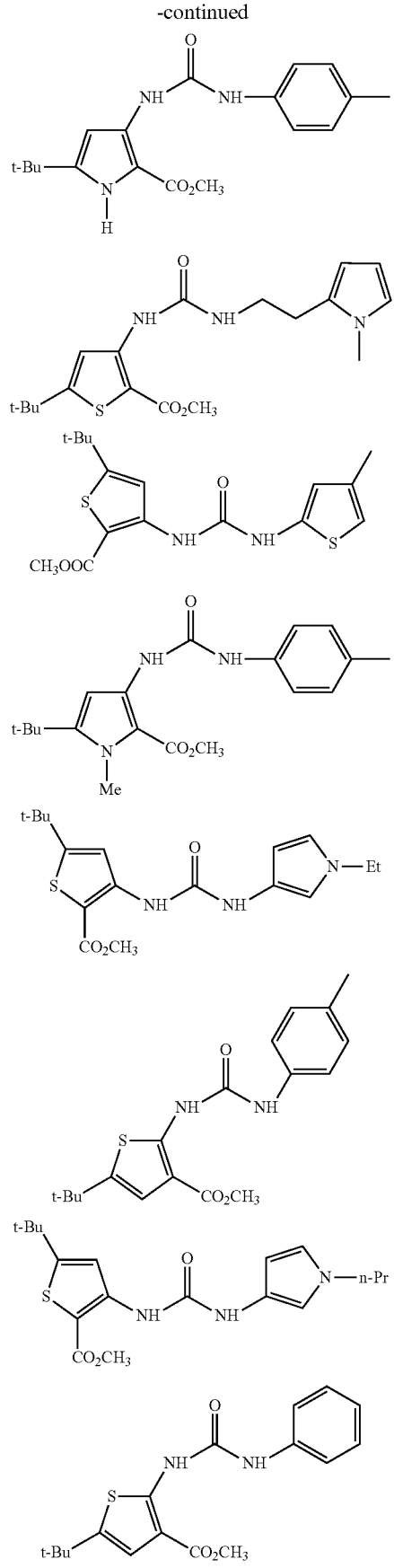

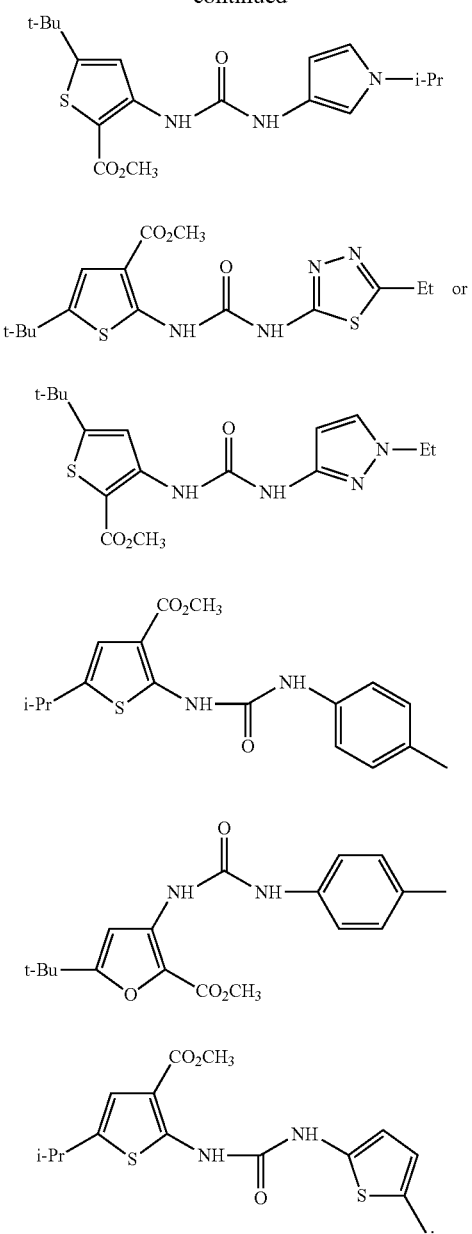

In some embodiments, the BRAF inhibitor is a compound as disclosed in PCT Publication No. WO 2010/111527, which is incorporated by reference herein. For example, the BRAF inhibitor can have a structure according to Formula I of PCT Publication No. WO 2010/111527.

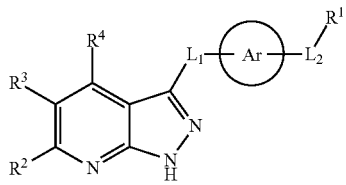

Formula I or a salt, a prodrug, a tautomer or an isomer thereof, wherein:
Ar is selected from the group consisting of:

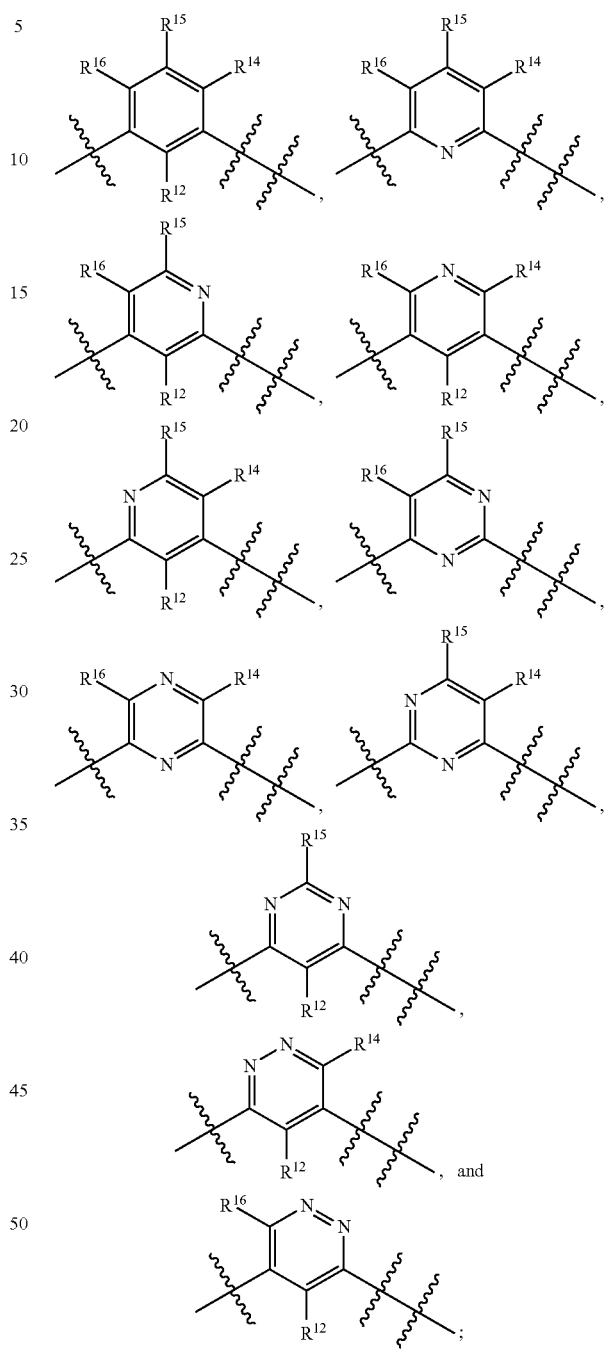

wherein $\stackrel{\xi}{\sim}$ indicates the point of attachment of Ar to Lj of Formula I and $\stackrel{\xi\xi}{\sim}$ indicates the point of attachment of Ar to L^ of Formula I;

L, is selected from the group consisting Of —C($R^5R^6$)—, —C(O)—, —C(S)—, —N($R^7$)—, —O—, —S—, —S(O)—, and —S(O)$_2$—;

L2 is selected from the group consisting of —N($R^8$)—C(O)—, —N($R^8$)—C(S)—, —N($R^8$)—S(O)—N($R^8$)—S(O)$_2$—, —N($R^8$)—C(O)—N($R^8$)—, —N($R^8$)—C(S)—N($R^8$)—, and —N($R^8$)—S(O)$_2$—N($R^8$)—;

R$^1$ is selected from the group consisting of optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

R$^2$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—R$^9$, —S—R$^{11}$, —N(R$^9$)—R$^{10}$, —C(O)—R$^{11}$, —C(S)—R$^{11}$, —C(O)—N(R$^9$R$^{10}$, —C(S)—N(R$^9$)—R$^{10}$, —C(O)—N(R$^{13}$)—OR$^9$, —C(S)—N(R$^{13}$)—OR$^9$, —C(O)—N(R$^{13}$)—S(O)$_2$—R$^{11}$, —C(S)—N(R$^{13}$)—S(O)$_2$—R$^{11}$, —C(O)—O—R$^9$, —S(O)—R$^{11}$, —S(O)$_2$—R$^{11}$, —S(O)—N(R$^9$)—R$^{10}$, —S(O)$_2$—N(R$^9$)—R$^{10}$, —S(O)$_2$—N(R$^{13}$)—C(O)R$^{11}$, —S(O)$_2$—N(R$^{13}$)—C(S)R$^{11}$, —N(R$^{13}$)—C(O)—R$^{11}$, —N(R$^{13}$)—C(S)—R$^{11}$, —N(R$^{13}$)—S(O)—R$^{11}$, —N(R$^{13}$)—S(O)$_2$—R$^{11}$, —N(R$^{13}$)—C(O)—N(R$^9$)—R$^{10}$, —N(R$^{13}$)—C(S)—N (R$^9$)—R$^{10}$, and —N(R$^{13}$)—S(O)$_2$—N(R$^9$)—R$^{10}$;

R$^3$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—R$^{17}$, —S—R$^{19}$, —N(R$^{17}$)—R$^{18}$, —C(O)—R$^{19}$, —C(S)—R$^{19}$, —C(O)—N (R$^{17}$R$^{18}$, —C(S)—N(R$^{17}$)—R$^{18}$, —C(O)—N(R$^{20}$)—OR$^{17}$, —C(S)—N(R$^{20}$)—OR$^{17}$, —C(O)—N(R$^{20}$)—S(O)$_2$—R$^{19}$, —C(S)—N(R$^{20}$)—S(O)$_2$—R$^{19}$, —C(O)—O—R$^{17}$, —S(O)—R$^{19}$, —S(O)$_2$—R$^{19}$, —S(O)—N(R$^{17}$)—R$^{18}$, —S(O)$_2$—N(R$^{17}$)—R$^{18}$, —S(O)$_2$—N(R$^{20}$)—C(O)R$^{19}$, —S(O)$_2$—N(R$^{20}$)—C(S)R$^{19}$, —N(R$^{20}$)—C(O)—R$^{19}$, —N(R$^{20}$)—C(S)—R$^{19}$, —N(R$^{20}$S(O)—R$^{19}$, —N(R$^{20}$S(O)$_2$—R$^{19}$, —N(R$^2$OC(O)—N(R$^{17}$)—R$^{18}$, —N(R$^{20}$)—C (S)—N(R$^{17}$)—R$^{18}$, and —N(R$^{20}$)—S(O)$_2$—N(R$^{17}$)—R$^{18}$;

R$^4$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—R$^{21}$, —S—R$^{23}$, —N(R$^{21}$)—R$^{22}$, —C(O)—R$^{23}$, —C(S)—R$^{23}$, —C(O)—N (R$^{21}$)—R$^{22}$, —C(S)—N(R$^{21}$)—R$^{22}$, —C(O)—N(R$^{24}$)—OR$^{21}$, —C(S)—N(R$^{24}$)—OR$^{21}$, —C(O)—N(R$^{24}$)—S(O)$_2$—R$^{23}$, —C(S)—N(R$^{24}$)—S(O)$_2$—R$^{23}$, —C(O)—O—R$^{21}$, —S(O)—R$^{23}$, —S(O)$_2$—R$^{23}$, —S(O)—N(R$^{21}$)—R$^{22}$, —S(O)$_2$—N(R$^{21}$)—R$^{22}$, —S(O)$_2$—N(R$^{24}$)—C(O)R$^{23}$, —S(O$_2$—N(R$^{24}$)—C(S)R$^{23}$, —N(R$^{24}$)—C(O)—R$^{23}$, —N(R$^{24}$)—C(S)—R$^{23}$, —N(R$^{24}$)—S(O)—R$^{23}$, —N(R$^{24}$)—S(O)$_2$—R$^{23}$, —N(R$^{24}$)—C(O)—N(R$^{21}$)—R$^{22}$, —N(R$^{24}$)—C(S)—N(R$^{21}$)—R$^{22}$, and —N(R$^{24}$)—S(O)$_2$—N (R$^{21}$)—R$^{22}$;

R$^5$ and R$^6$ are independently selected from the group consisting of hydrogen, fluoro, —OH, —NH$_2$, lower alkyl, lower alkoxy, lower alklylthio, mono-alky lamino, di-alkylammo, and —N(R$^{25}$)—R$^{26}$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy. fluoro substituted lower alkoxy, lower alkylthio, fluoro substituted lower alkylthio, mono-alkylamino, di-alkylamino, and cycloalkylammo; or R$^5$ and R$^6$ combine to form a 3-7 membered monocyclic cycloalkyl or 5-7 membered monocyclic heterocycloalkyl, wherein the 3-7 membered monocyclic cycloalkyl or 5-7 membered monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylammo, di-alkylamino, and cycloalkylammo, R$^7$, R$^{13}$, R$^{20}$, and R$^{24}$ are independently selected from the group consisting of hydrogen, optionally substituted lower alkyl, optionally substituted cycloalkyl, optionally substituted heterocycloalkyl, optionally substituted aryl, optionally substituted heteroaryl, —C(O)—R$^{27}$, —C(S)—R$^{27}$, —S(O)—R$^{27}$, —S(O)$_2$—R$^{27}$, —C(O)—N(H)—R$^{27}$, —C(S)—N(H)—R$^{27}$, and —S(O)$_2$—N(H)—R$^{27}$, R$^8$ at each occurrence is independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylammo, di-alkylamino, fluoro substituted di-alkylamino, and —N(R$^{25}$)—R$^{26}$, R$^{12}$, R$^{14}$, R$^{15}$, and R$^{16}$ are independently selected from the group consisting of hydrogen, halogen, optionally substituted lower alkyl, —N(R$^{28}$)—R$^{29}$, —O—R$^{28}$, and —S—R$^{30}$, R$^{11}$, R$^{19}$ and R$^{23}$ are independently selected from the group consisting of optionally substituted lower alkyl, optionally substituted lower alkenyl. optionally substituted lower alkynyl, optionally substituted cycloalkyl, optionally substituted heterocycloalkyl, optionally substituted aryl, and optionally substituted heteroaryl, R$^9$, R$^{10}$, R$^{17}$, R$^{18}$, R$^{21}$ and R$^{22}$ are independently selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

R$^{25}$ and R$^{26}$ at each occurrence combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

R$^{27}$ at each occurrence is independently selected from the group consisting of optionally substituted lower alkyl, optionally substituted cycloalkyl, optionally substituted heterocycloalkyl, optionally substituted aryl, and optionally substituted heteroaryl;

R$^{28}$ and R$^{29}$ at each occurrence are independently hydrogen or optionally substituted lower alkyl; and R$^{30}$ at each occurrence is optionally substituted lower alkyl.

In some embodiments, the BRAF inhibitor is a compound having the formula disclosed in U.S. Pat. No. 7,329,670, which is incorporated by reference herein. For example, the BRAF inhibitor can have the following structure

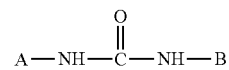

wherein B is generally an unsubstituted or substituted, up to tricyclic, aryl or heteroaryl moiety with up 30 carbon atoms with at least one 5 or 6 member aromatic structure containing 0-4 members of the group consisting of nitrogen, oxygen and sulfur. A is a heteroaryl moiety.

In some examples of the presence disclosure, the BRAF inhibitor is GDC 0789 (Genentech):

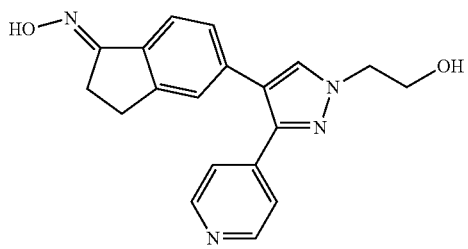 [SMILES: OCCn1cc(-c2ccc3c(c2)CC/C3=N\O)c(-c2ccncc2)n1]

In other examples, the inhibitor is PD-325901, XL518, PD-184352, PD-318088, AZD6244 or CI-1040 (see PCT Publication No. WO 2009/047505, incorporated herein by reference).

In further examples, the BRAF inhibitor can be an antibody that specifically binds BRAF, or an antigen binding fragment thereof. This includes monoclonal antibodies and antigen binding fragments that specifically bind BRAF. The BRAF inhibitor can also be an inhibitory RNA, such as, but not limited to, anti-sense RNA, small inhibitor RNA, and shRNA.

Methods of Treatment

Methods are provided herein for treating a subject diagnosed with a tumor that expresses a mutated BRAF. The methods include administering to the subject (1) a therapeutically effective amount of an antibody or antigen binding fragment thereof that specifically binds high molecular weight melanoma associated antigen (HMW-MAA), and/or a nucleic acid encoding the antibody or antigen binding fragment; and (2) a therapeutically effective amount of a BRAF inhibitor, thereby treating the cancer in the subject. Thus, the use of (1) an antibody or antigen binding fragment thereof that specifically binds high molecular weight melanoma associated antigen (HMW-MAA), and/or a nucleic acid encoding the antibody or antigen binding fragment; and (2) a therapeutically effective amount of a BRAF inhibitor for the treatment of a tumor is provided herein.

These use of a BRAF inhibitor in combination with an antibody or antigen binding fragment thereof that specifically binds HMW-MAA provide an unexpectedly superior result for the treatment of any tumor, wherein cells in the tumor comprise a BRAF mutation. In other embodiments, the BRAF mutation is a V600E mutation. In other embodiments, the BRAF mutation is R462I, I463S, G464E, G464V, G466A, G466E, G466V, G469A, G469E, N581S, E585K, D594V, F595L, G596R, L597V, T599I, V600D, V600E, V600K, V600R K601E, and A728V. In further embodiments the BRAF mutation is in one of two regions: the glycine-rich P loop of the N lobe and the activation segment and flanking regions. The cells in the tumor can have more than one BRAF mutation.

In additional embodiments, the subject has a primary or secondary resistance to the BRAF inhibitor. A subject that does not respond initially to a BRAF inhibitor has primary resistance. A subject that initially responds to the BRAF inhibitor, but then ceases to respond, has secondary resistance. In some examples, the subject responds for one, two, three, four, five, six, seven, eight, nine, ten, eleven or twelve months, but then does not respond to the BRAF inhibitor. Thus, the methods can include selecting a subject with a resistance to a BRAF inhibitor, such as selecting a subject with primary resistance to the BRAF inhibitor or secondary resistance to the BRAF inhibitor.

Thus, in some embodiments, the method includes selecting a subject that has secondary resistance to a BRAF inhibitor, such as a subject with secondary resistance to a BRAF inhibitor that has a tumor, such as melanoma. In other embodiments, the method includes selecting a subject with primary resistance to a BRAF inhibitor, such as a subject with primary resistance to a BRAF inhibitor that has a tumor, such as melanoma.

The disclosed methods can also be used to prevent metastasis or decrease the number of micrometastases, such as micrometastases to regional lymph nodes. Disclosed herein are methods to treat a subject diagnosed with a tumor, such as a melanoma. Melanoma includes spreading melanoma, nodular melanoma, acral lentiginous melanoma, and lentigo maligna (melanoma). However, the methods disclosed herein can also be used to treat other cancers, such breast cancer, prostate cancer, ovarian cancer, colon cancer, stomach cancer, pancreatic cancer, glioma, chordoma, chondrosarcoma, glioma, colon cancer, or a squamous cell carcinoma. Squamous cells carcinomas include, but are not limited to head and neck squamous cell carcinoma, and squamous cell cancers of the skin, lung, prostate, esophagus, vagina and cervix. The methods disclosed herein can also be used to breast cancer, head and neck squamous cell carcinoma, renal cancer, lung cancer, glioma, bladder cancer, ovarian cancer or pancreatic cancer, wherein cells of the cancer express HMW-MAA. The methods also can be used to treat non-Hodgkin lymphoma, colorectal cancer, papillary thyroid carcinoma, non-small cell lung carcinoma, and adenocarcinoma of lung. Thus, the methods can include selecting a subject with a tumor that expresses HMW-MAA.

A variety of different types of melanoma may be treated in accordance with the present methods including, such as superficial spreading melanoma, nodular malignant melanoma, acral lentiginous melanoma, lentiginous malignant melanoma, and mucosal lentiginous melanoma. The primary melanoma may also be cutaneous or extracutaneous. Extracutaneous primary malignant melanomas include ocular melanoma and clear-cell sarcoma of the soft tissues. Additional indications include rare melanomas or precancerous lesions where relevance of RTK targets may be implicated. The present methods are also useful in the treatment of melanoma that has metastasized.

A therapeutically effective amount of the agents will depend upon the severity of the disease and the general state of the patient's health. A therapeutically effective amount of the antibodies or antigen binding fragments thereof (or nucleic acids encoding the antibody or antigen binding fragment) and BRAF inhibitor is that which provides either a reduction in tumor burden, decreased metastatic lesions and/or subjective relief of a symptom(s) or an objectively identifiable improvement as noted by the clinician or other qualified observer.

The antibody or antigen binding fragment can be administered in the same formulation or separately. They can be given at the same time or a different time (simultaneously or sequentially), but sufficiently concurrently to have the beneficial effect disclosed herein. Compositions are provided herein that include a carrier and one or more of the antibodies that specifically bind HMW-MAA and/or antigen binding fragments thereof, in combination with a BRAF inhibitor. Compositions comprising immunoconjugates or immunotoxins of these antibodies are also provided. The compositions can be prepared in unit dosage forms for administration to a subject. The amount and timing of administration are at the discretion of the treating physician to achieve the desired purposes.

The antibody (or a nucleic acid encoding the antibody) and/or BRAF inhibitor can be formulated for systemic or local (such as intra-tumor) administration. In one example, the antibodies and/or BRAF inhibitor is formulated for parenteral administration, such as intravenous administration. In another example, the antibodies, antigen binding fragments, nucleic acid and/or one or more BRAF inhibitors are formulated for topical administration, subcutaneous or intradermal administration. A BRAF inhibitor and/or and antibody or antigen binding fragment described above (or a nucleic acid encoding the antibody or antigen binding fragment) can be delivered transdermally via, for example, a transdermal delivery device or a suitable vehicle or, such in an ointment base, which may be incorporated into a patch for controlled delivery. Such devices are advantageous, as they may allow a prolonged period of treatment relative to, for example, an oral or intravenous medicament. Examples of transdermal delivery devices may include, for example, a patch, dressing, bandage or plaster adapted to release a compound or substance through the skin of a patient.

The compositions for administration can include a solution of the antibodies that specifically bind HMW-MAA (or nucleic acids encoding these antibodies) and/or BRAF inhibitor(s) dissolved or suspended in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies can be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Compositions for administering BRAF inhibitors are known in the art. Suitable BRAF inhibitors and pharmaceutical formations including these inhibitors are disclosed for example, in PCT Publication No. WO2009047505A2, PCT Publication No. WO03086467A1, U.S. Published Patent Application US20050176740A1, U.S. Pat. Nos. 6,187,799, 7,329,670, PCT Publication No. WO2009143024A2, PCT Publication No. WO2010104945A1, PCT Publication No. WO2010104973A1, PCT Publication No. WO2010111527A1, U.S. Published Patent Application No. 20090286783A1 and PCT Publication No. WO2009152087A1, all of which are incorporated by reference herein.

The antibody or antigen binding fragment thereof that specifically binds HMW-MAA (or a nucleic acid encoding the antibody or antigen binding fragment) and the BRAF inhibitors can be administered to slow or inhibit the growth of cells, such as cancer cells. In these applications, a therapeutically effective amount of an antibody is administered to a subject in an amount sufficient to inhibit growth, replication or metastasis of cancer cells, or to inhibit a sign or a symptom of the cancer. In some embodiments, the compositions are administered to a subject to inhibit or prevent the development of metastasis, or to decrease the size or number of metasases, such as micrometastases, for example micrometastases to the regional lymph nodes (Goto et al., *Clin. Cancer Res.* 14(11): 3401-3407, 2008).

These compositions disclosed herein can be administered in conjunction with another chemotherapeutic agent, either simultaneously or sequentially. Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Methods of treating melanoma can further include administering one or more additional anti-cancer drugs for the treatment of melanoma with a compound as defined herein. For example, anti-cancer drugs for the treatment of melanoma, especially metastatic melanoma, may be selected from alkylating anti-cancer drugs such as dacarbazine, temozolomide, mechlorethamine, and nitrosoureas such as carmustine, lomustine, and fotemustine; taxanes, such as paclitaxel and docetaxel; vinca alkaloids, such as vinblastine; topoisomerase inhibitors such as irinotecan; thalidomide; anti-cancer antibiotics such as streptozocin and dactinomycin; or platinum anti-cancer drugs, such as cisplatin and carboplatin. Compounds of the invention may be added to polychemotherapeutic regimes such as the Dartmouth regime, CVD (cisplatin. vinblastine, and dacarbazine) and BOLD (bleomycin, vincristine, lomustine, and dacarbazine). In some embodiments, the anti-cancer drugs are selected from interferons such as, but not limited to, interferon alpha-2a, interferon alpha-2b, pegylated interferons such as pegylated interferon alpha-2b. Interleukins such as interleukin-2 may also be used in combination with compounds disclosed herein.

In the methods of treating melanoma described herein, the therapeutically effective amount of the compound can range from about 0.25 mg/kg to about 30 mg/kg body weight of the subject. In some embodiments, the therapeutically effective amount of the compound can range from about 0.5 mg/kg to about 30 mg/kg, from about 1 mg/kg to about 30 mg/kg, from about 1 mg/kg to about 25 mg/kg, from about 1 mg/kg to about 15 mg/kg, or from about 1 or 2 mg/kg to about 10 mg/kg. In other embodiments, the amount of the compound administered to the subject ranges from about 25 to about 1500 mg/day and, preferably, from about 100 or 200 mg/day to about 500 or 600 mg/day.

Treatment may also include administering the pharmaceutical formulations of the present methods in combination with other therapies. For example, a pharmaceutical formulations including the antibody and BRAF inhibitor may be administered before, during, or after a surgical procedure and/or radiation therapy.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with the antibody and the BRAF inhibitor. Examples of useful COX-II inhibitors include CELEBREX™ (alecoxib), valdecoxib, and rofecoxib. Examples of useful matrix metalloproteinase inhibitors are described in PCT Publication No. WO 96/33172 (published Oct. 24, 1996), PCT Publication No. WO 96/27583 (published Mar. 7, 1996), European Patent Application No. 97304971.1 (filed Jul. 8, 1997), European Patent Application No. 99308617.2 (filed Oct. 29, 1999), PCT Publication No. WO 98/07697 (published Feb. 26, 1998), PCT Publication No WO 98/03516 (published Jan. 29, 1998), PCT Publication No WO 98/34918 (published Aug. 13, 1998), PCT Publication No WO 98/34915 (published Aug. 13, 1998), PCT Publication No WO 98/33768 (published Aug. 6, 1998), PCT Publication No WO 98/30566 (published Jul. 16, 1998), European Patent Publication 606,046 (published Jul. 13, 1994), European Patent Publication 931,788 (published Jul. 28, 1999), PCT Publication No WO 90/05719 (published May 31, 1990), PCT Publication No WO 99/52910 (published Oct. 21, 1999), PCT Publication No WO 99/52889 (published Oct. 21, 1999), PCT Publication No WO 99/29667 (published Jun. 17, 1999), PCT International Application No. PCT/IB98/01113 (filed Jul. 21, 1998), European Patent Application No. 99302232.1 (filed Mar. 25, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997). In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy) -benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy) -benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy) -benzenesulfonylamino]-tetrahydro-furan-3-carboxylic acid hydroxyamide; and pharmaceutically acceptable salts and solvates of said compounds.

The antibody or antigen binding fragment that specifically bind HMW-MAA (or nucleic acid encoding the antibody or antigen binding fragment) and the BRAF inhibitor can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in PCT Publication Nos. WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents also include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds endoplasmin. VEGF inhibitors are described in, for example in PCT Publication No. WO 99/24440 (published May 20, 1999), PCT International Application PCT/IB99/00797 (filed May 3, 1999), PCT Publication No. WO 95/21613 (published Aug. 17, 1995), PCT Publication No. WO 99/61422 (published Dec. 2, 1999), U.S. Pat. No. 5,834,504 (issued Nov. 10, 1998), PCT Publication No. WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), PCT Publication No. WO 99/10349 (published Mar. 4, 1999), PCT Publication No. WO 97/32856 (published Sep. 12, 1997), PCT Publication No. WO 97/22596 (published Jun. 26, 1997), PCT Publication No. WO 98/54093 (published Dec. 3, 1998), PCT Publication No. WO 98/02438 (published Jan. 22, 1998), WO 99/16755 (published Apr. 8, 1999), and PCT Publication No. WO 98/02437 (published Jan. 22, 1998). Other examples of some specific VEGF inhibitors are IM862 (Cytran Inc.); anti-VEGF monoclonal antibody of Genentech, Inc.; and angiozyme, a synthetic ribozyme from Ribozyme and Chiron. These and other VEGF inhibitors can be used in conjunction with the antibodies, antigen binding fragments, and the BRAF inhibitor.

ErbB2 receptor inhibitors, such as GW-282974 (Glaxo Wellcome pic), and the monoclonal antibodies AR-209 (Aronex Pharmaceuticals Inc.) and 2B-1 (Chiron), can furthermore be combined with the antibodies, antigen binding fragments and BRAF inhibitor, for example those indicated in PCT Publication No. WO 98/02434 (published Jan. 22, 1998), PCT Publication No. WO 99/35146 (published Jul. 15, 1999), PCT Publication No. WO 99/35132 (published Jul. 15, 1999), PCT Publication No. WO 98/02437 (published Jan. 22, 1998), PCT Publication No. WO 97/13760 (published Apr. 17, 1997), PCT Publication No. WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors of use are also described in U.S. Provisional Application No. 60/117,341, filed Jan. 27, 1999, and in U.S. Provisional Application No. 60/117,346, filed Jan. 27, 1999.

For the treatment of cancer, such as melanoma, breast cancer or colon cancer, the antibody or antigen binding fragment that specifically bind HMW-MAA (or nucleic acid encoding the antibody or antigen binding fragment) and a BRAF inhibitor can be used with surgical treatment, or with another therapeutic including dacarbazine (also termed DTIC), or interleukin-2 (IL-2) or interferon, such as interferon (IFN). For the treatment of a superficial melanoma, the antibody or antigen binding fragment that specifically bind HMW-MAA (or nucleic acid encoding the antibody or antigen binding fragment) and a BRAF inhibitor can be used in conjunction with Imiquimod. However, for the treatment of another cancer, such as head and neck squamous cell carcinoma, the antibody or antigen binding fragment that specifically bind HMW-MAA (or nucleic acid encoding the antibody or antigen binding fragment) and a BRAF inhibitor can be used in conjunction with surgery, radiation therapy, chemotherapy, other antibodies (such as cetuximab and bevacizumab) or small-molecule therapeutics (such as erlotinib). One of skill in the art can readily determine surgical procedures and additional chemotherapeutic agents of use.

Single or multiple administrations of the compositions are administered depending on the dosage and frequency as required and tolerated by the patient. In any event, the composition should provide a sufficient quantity of at least one of the antibodies (or antigen binding fragments thereof) and BRAF inhibitor to effectively treat the patient. The dosage can be administered once but may be applied periodically until either a therapeutic result is achieved or until side effects warrant discontinuation of therapy. The subject can be treated at regular intervals, such as daily, weekly, biweekly, or monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the antibody compositions disclosed herein. Various degradable and non-degradable polymeric matrices for use in controlled drug delivery are known in the art (Langer, Accounts Chem. Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic molecules are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

The disclosure is illustrated by the following non-limiting Examples.

EXAMPLES

The treatment of metastatic melanoma is changing rapidly due to the great success in translational research from bench to bedside. PLX4032 (RG7204, Plexxikon,) is a selective V600E mutated BRAF inhibitor. A response rate of 70% in 32 BRAF mutated advanced melanoma patients treated by PLX4032 was reported in the phase II study (Flaherty et al, *N Engl J Med* 363:809-819, 2010). Although the significant clinical activity of BRAF selective inhibitors is a major breakthrough in the treatment of this disease, there are many hurdles to overcome to optimize this targeted therapy approach (Flaherty and McArthur, *Cancer* 116:4902-4913, 2010). Some patients did not respond (primary resistance). Most patients had partial responses. Moreover, the median duration of response is approximately only 8 months (secondary resistance).

The next urgent clinical goal is to identify rational therapy to obtain complete response and to improve the longevity of initial response to BRAF-inhibitor (BRAF-I). The chondroitin sulfate proteoglycan 4 (CSPG4, also known as High-Molecule Weight-Melanoma Associated Antigen, HMW-MAA) is a membrane-bound proteoglycan that consists of an N-linked 280 kDa glycoprotein and a 450 kDa chondroitin sulfate proteoglycan; it is highly expressed on the membrane of melanoma cells (Campoli et al., *Clin Cancer Res* 16:11-20, 2010); it is expressed in at least 80% of primary and metastatic melanoma lesions with limited inter- and intra-lesional heterogeneity; it has a restricted distribution in normal tissues (Campoli et al., *Clin Cancer Res* 16:11-20, 2010); and it plays an important role in the activation of several signaling pathways which are known to be important in tumor cell proliferation, survival and migration as well as in tumor progression (Wang et al, *Curr Mol Med* 10:419-429, 2010; Yang et al, *Cancer Res* 69:7538-7547, 2009; Yang et al., *J Cell Biol* 165:881-891, 2004). HMW-MAA(CSPG4) is expressed by breast cancer stem cells (CSC). A HMW-MAA (CSPG4)-specific mouse mAb, 225.28, inhibited the growth, adhesion, and/or migration and survival of triple negative breast cancer cells in vitro and in vivo.

Example 1

Effect of mAb 225.28

Figure 2:
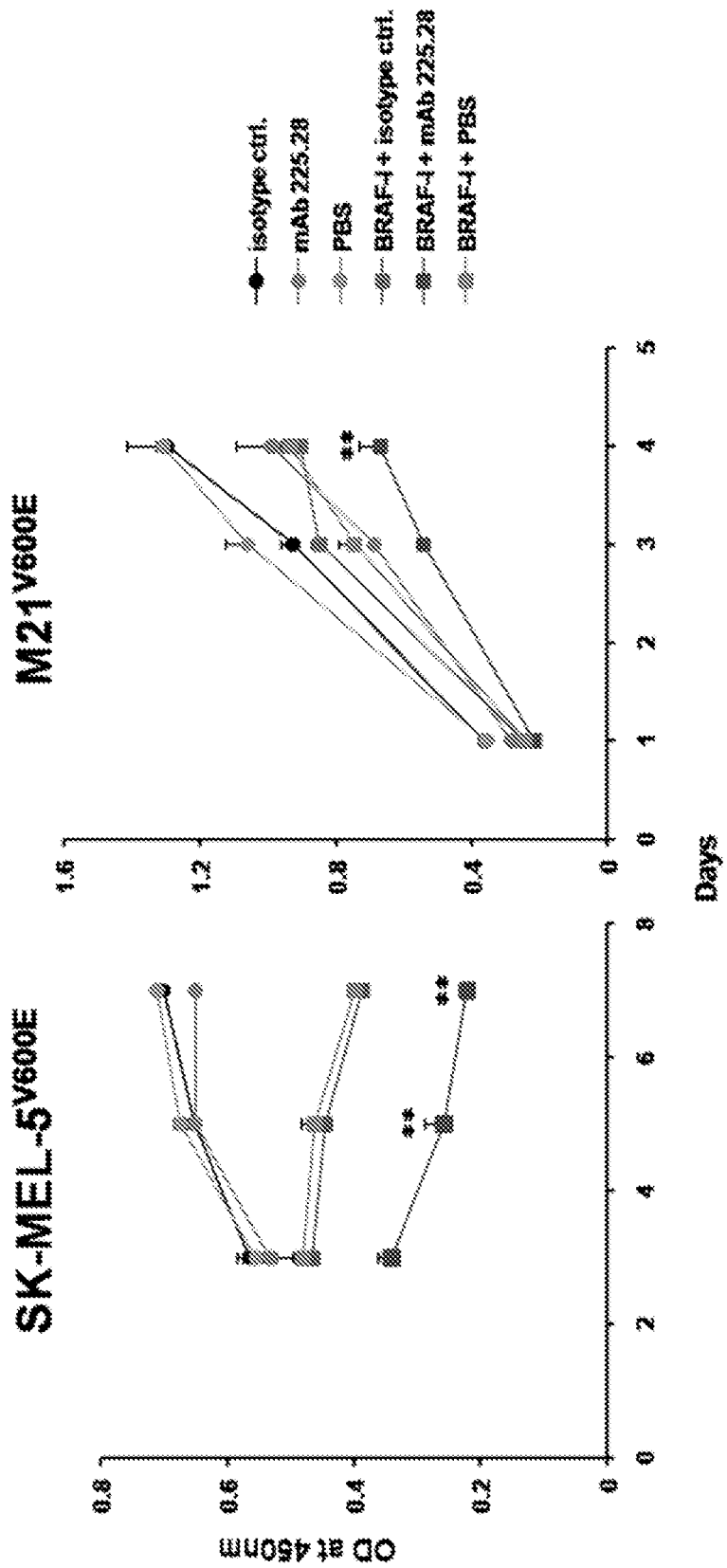
FIG. 2. Inhibition of melanoma cell growth by combination of BRAF-inhibitor (BRAF-I) PLX4720 with mAb 225.28 in vitro. Human V600E BRAF mutated melanoma cells SK-MEL-5 and M21 were treated as indicated. The dose of all mAb is 0.25 mg/ml, and the dose of BRAF-I is 5 μM. MTT assay was performed to determine cell growth of each treatment condition. Error bar: standard deviation. BRAF-I+Isotype vs. BRAF-I+mAb225.28 **p value<0.01.
Figure 3:
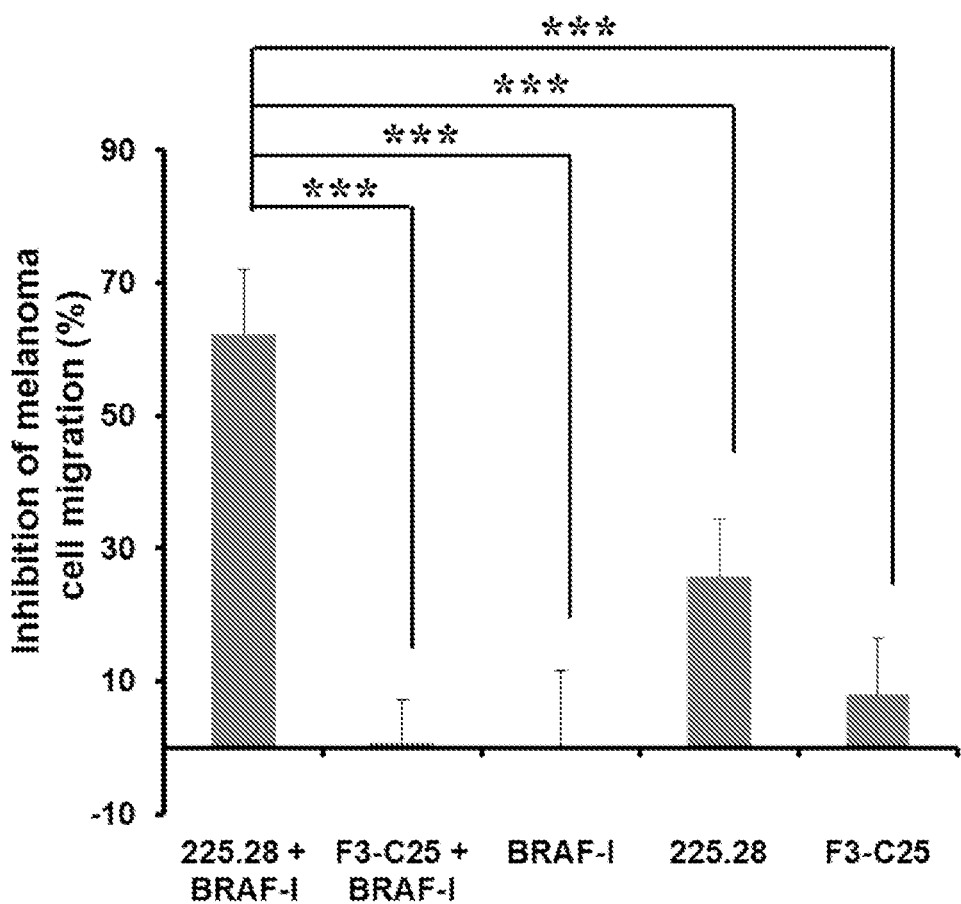
FIG. 3. Inhibition by CSPG4-specific mAb 225.28 combined with BRAF inhibitor PLX4720 of M21R cells migration. M21R cells were incubated in RPMI 1640 medium containing 1% FCS with mAb 225.28, isotype control mAb, BRAF Inhibitor PLX4720 combined with mAb 225.28, BRAF-I combined with isotype control mAb, or BRAF-I in a 24-trans-well plate ($2.5 \times 10^4$ per well) for 3 days in a migration assay. Cells incubated in RPMI 1640 medium containing 1% FCS was used as a reference for 100% cell migration. The results are expressed as % inhibition of migration, utilizing the values obtained in RPMI 1640 medium containing 1% FCS without mAb as a reference. *p value<0.05; **p value<0.01.
Figure 4:
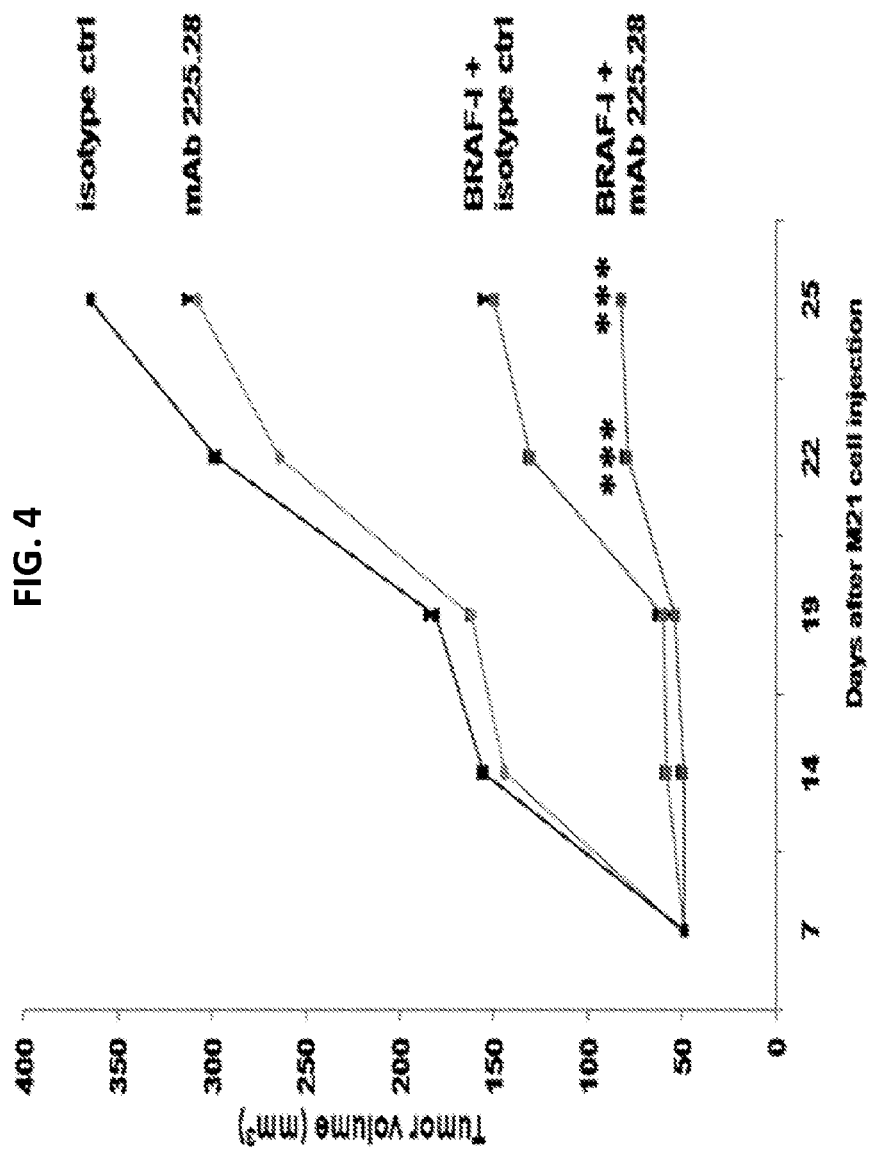
FIG. 4. Inhibition of melanoma cell growth in vivo by combination of BRAF-I PLX4720 and mAb 225.28. Human melanoma cells $M21^{V600E}$ ($2 \times 10^6$/mouse) were subcutaneously (s.c.) injected to 8 SCID mice on day 0. On day 7, when the primary tumor formed, all mice were divided by stratified randomization into 4 groups of 2 mice each and each group was started to receive different treatment as indicated. All mAb was given i.v., 100 µg/mouse, twice weekly. BRAF-I was given orally, 20 mg/kg once daily. Error bars: standard deviation. BRAF-I+isotype vs. BRAF-I+mAb225.28: *** p value<0.001.

HMW-MAA (CSPG4)-blocking mAb 225.28 could effectively inhibit the in vitro and in vivo activation of FAK, RAS (upstream of BRAF in RAS-RAF-MEK-ERK kinase pathway), ERK1/2, AKT, and PKCa in tumor cells (FIG. 1) (Wang et al., *J Natl Cancer Inst* 102:1496-1512, 2010). An enhancement of response in the magnitude and duration of BRAF-I could be achieved by the combination of BRAF-I with the anti-HMW-MAA (CSPG4) monoclonal antibody (mAb) 225.28, which targets, on its own, multiple signaling pathways including but not limited to RAS-ERK and PI3-AKT signaling important for cell growth, migration and survival (FIG. 1) (Wang et al., *J Natl Cancer Inst* 102:1496-1512, 2010). This combination of BRAF-I PLX4720 and anti-HMW-MAA (CSPG4) mAb 225.28 is more effective than either agent alone in inhibiting V600E mutated melanoma cell growth in vitro (FIG. 2, FIG. 3) and in vivo (FIG. 4).

It was determined that melanoma cells that have a BRAF mutation also express HMW-MAA (CSPG4).

TABLE 1

CSPG4 expression by mutated BRAF$^{V600E}$ human melanoma cell lines.

| Cell Lines | BRAF status | CSPG4 % * | (MFI) |
|---|---|---|---|
| 526 | V600E | 78.4 | (20.2) |
| 677 | V600E | 93.0 | (55.8) |
| 1287 | V600E | 99.9 | (116.8) |
| Mel624 | V600E | 88.2 | (130.0) |
| M233 | V600E | 40.8 | (274.3) |
| SK-MEL-5 | V600E | 99.6 | (275.3) |
| MV3 | Wild type | 99.7 | (581.1) |
| SK-MEL-37 | V600E | 99.9 | (279.8) |
| 1495 | V600E | 80.0 | (436.9) |
| Colo38 | V600E | 99.8 | (493.4) |
| SK-MEL-28 | V600E | 99.8 | (572.4) |
| WM1158 | V600E | 99.8 | (586.3) |
| SK-MEL-19 | V600E | 99.9 | (606.9) |
| UACC-257 | V600E | 99.9 | (890.3) |
| M21 | V600E | 99.9 | (917.4) |
| 836 | V600E | 99.4 | (1211.3) |

Table 1. CSPG4 expression by V600E mutated BRAF human melanoma cell lines. Flow cytometry analysis of CSPG4 expression by melanoma cell lines using anti-CSPG4 mAb 225.28 and PE-conjugated anti-mouse IgG.

Table 1. HMW-MAA (CSPG4) Expression by V600E Mutated BRAF Human Melanoma Cell Lines. Flow cytometry analysis of HMW-MAA (CSPG4) expression by melanoma cell lines using anti-HMW-MAA (CSPG4) mAb 225.28 and PE-conjugated anti-mouse IgG. 526, 677, 1287, Me1624; low CSPG4 expression; M233, SK-MEL-5, MV3, SK-MEL-37, 1495, Colo 38; medium CSPG4 expression and SK-MEL-28, WM1158, SK-MEL-19, UACC-257, M21, 836; high CSPG4 expression, as determined by mean fluorescence intensity (MFI).
*Percentage of cells that express CSPG4.

Example 2

Determination of Doses for In Vitro Studies

A dose-dependent response analysis is used to identify optimal and suboptimal doses of BRAF-I and anti-CSPG4 mAb 225.28, respectively, in each of the 6 cell lines. The cell growth rate is measured by MTT assay detailed below. BRAF-I PLX4720 is used at doses of 0.01, 0.02, 0.04, 0.08, 0.16, 0.30, 0.63, 1.25, 2.5, 5, 10 μm to treat each cell lines for 1, 3 and 5 days. In an independent experiment, anti-HMW-MAA (CSPG4) mAb 225.28 is used at doses of 0.1, 0.25, 0.5 mg/ml to treat each cell lines for 1, 3 and 5 days. Depending on the extent of inhibition achieved by optimal (gives the highest rate of inhibition) and suboptimal (gives lower, next-highest inhibition) doses, an "optimized" dose, is used, either optimal or suboptimal of each agent which gives 50-70% inhibition alone to allow performing combination therapy.

Example 3

Combination Therapy with BRAF-I PLX4720 and Anti-CSPG4 mAb 225.28 Controls Melanoma Cell Growth and Migration To measure cell growth in vitro, cells are seeded ($2.5 \times 10^3$ cells per well) in a 96-well plate (Becton Dickinson and Company) and treated with 5 different regimens as follows: PLX 4720, mAb225.28, PLX4720+mAb225.28, PLX4720+ Isotype control mAb (in 200 μL RPMI 1640 medium/per well), respectively or left untreated for 24, 72, 120 hours at 37° C. in a 5% $CO_2$ atmosphere. The identified optimized doses in Example 1 of PLX 4720 and the anti-HMW-MAA (CSPG4) mAb 225.28 or isotype control mAb are used. During the last 4-hour incubation, living cells convert the MTT tetrazolium component Methylthiazolyldiphenyl-tetrazolium bromide (Sigma) of the Dye Solution into a formazan product, which can be read at 540 nm by a plate ELISA reader. The results are expressed as percent inhibition of cell growth using the untreated cells as a 100% reference. To measure cell migration, cells are seeded ($5.0 \times 10^4$ per well) in the top chamber of a 24-Transwell plate (8-1 μm pore size; BD Biosciences) and treated as described above. All bottom chambers of the Transwell plate are filled with serum-free RPMI 1640 medium (600 μL per well) containing fibronectin (10 μg/mL; Sigma). At the end of day 2, migrated cells are stained with HEMA 3 stain set (Fisher Scientific) according to the manufacturer's instructions. The nonmigrated cells on the top side of the filter are removed by scrubbing twice with cotton tipped swab. The migrated cells on the bottom side of six randomly selected fields per well are then imaged and counted using a Zeiss Inverted Fluorescence Microscope (AxioVision Software, Carl Zeiss MicroImaging GmbH). The results are expressed as percent inhibition of migration using the number of migrated cells untreated as a 100% reference. All experiments are performed three independent times in triplicates.

Example 4

Combination Therapy with BRAF-I PLX4720 and Anti-HMW-MAA (CSPG4) mAb 225.28 is More Effective than Either Agent Alone in Inducing Melanoma Cell Apoptosis To measure cell apoptosis in vitro, cells are seeded ($5.0 \times 10^4$ cells per well) in a 96-well plate and treated with 5 different regimens as described above for 2, 6 and 24 hours. Cells are then subjected to staining simultaneously with FITC-Annexin V (green fluorescence) (BD Biosciences) and the non-vital dye propidium iodide (red fluorescence) (BD Biosciences), which allows bivariate analysis to discriminate intact cells (FITC PI), early apoptotic (FITC⁺PI⁻) and late apoptotic or necrotic cells (FITC⁺PI⁺). All experiments are performed three independent times.

To investigate the mechanisms of action underlying the effects on cell growth, migration and apoptosis, cells treated as described above are lysed for examining the changes in the level of total and activated signaling protein molecules, such as FAK, RAS, BRAF, ERK1/2, PI3, AKT, PKCα by Western blot. The significance of the difference in cell growth, migration, apoptosis and the level of signaling molecules are analyzed using the Student T test.

The primary resistance of melanoma cells to BRAF-I can be reversed and the secondary resistance of melanoma cells to BRAF-I can be delayed/prevented by targeting multiple signaling pathways with BRAF-I and anti-CSPG4 antibody. The M233$^{V600E}$ cell line is naturally, i.e., primarily resistant to BRAF-I (Sondergaard et al., *J Transl Med* 8:39, 2010). In addition to M233 cell line, in order to obtain at least one more BRAF-I primary resistant cell line, additional V600E mutated human melanoma cell lines are screened using a cell growth MTT assay. It is determined that the combination therapy can reverse their resistance to BRAF-I in these two primary resistant cell lines in cell growth assays. Furthermore, the cell lines M21$^{V600E}$ and SK-MEL-5$^{V600E}$ are used, both of which are BRAF-I sensitive (FIG. 2) to confirm that secondary resistance can be delayed or prevented in the presence of anti-CSPG4 mA225.28 in cell growth assays.

Example 5

V600E Mutated Human Melanoma Cell Lines and Resistance to PLX4720

Several V600E mutated human melanoma cell lines are tested to identify the cell lines which maintain the same growth rate at days 1, 3 and 7 in the presence and absence of BRAF-I PLX4720 (or PLX4320) at 5 μM in MTT assays. The identified cell lines, which are primary resistant to BRAF-I are confirmed with a higher dose (10 μM) of PLX4720 in cell growth assays.

The cells are treated with BRAF-I PLX4720 and anti-HMW-MAA (CSPG4) mAb 225.28 to determine that primary resistance of human melanoma cell lines to BRAF-I PLX4720 (or PLX4320) is affected by the combination therapy. In addition to cell line M233$^{V600E}$, the additional primary resistant cell lines are treated in several different regimens and then cell growth, migration and apoptosis is measured. Combination therapy affects the growth, migration and apoptosis of the cell lines.

It is also determined that combination treatment with BRAF-I PLX4720 (or PLX4320) and anti-CSPG4 mAb 225.28 delays and/or prevents secondary resistance of human melanoma cell lines to BRAF-I PLX4720 (or PLX4320). It has been determined that V600E mutated melanoma cell lines, which are sensitive to BRAF-I in vitro treatment, became resistant, i.e., secondary resistant, to PLX4720 (or PLX4320) after 3-4 week of in vitro treatment with increasing doses (2.5-10 μM) of PLX4720 (or PLX4320).

The cells (4×10⁵/well) are cultured in a 6-well plate containing 2 ml of RPMI 1640 medium supplemented with 10% FBS and 2.5 μM of PLX-4720 (or PLX4320). Medium is changed every 4 days. On day 8, the dose of PLX4720 (or PLX4320) is increased to 5 μM. Cells are cultured under these conditions for 12 days changing the medium every 4 days. Then the dose of PLX4720 (or PLX4320) is increased to 10 μM, changing the medium every 3 days. Cells are cultured until resistant colonies appear (around 3-4 weeks). Cells are tested for resistance to BRAF-I by testing their growth in the presence of 10 μM of PLX4720 (or PLX4320), using the MTT assay. Simultaneously, cells in one well will be set up in the exact same way except adding anti-CSPG4 mAb 225.28 every 3-4 days at its optimal dose identified as described above. In the control well, everything is not changed but only anti-HMW-MAA (CSPG4) mAb 225.28 is replaced with the isotype control mAb. The cells, in the presence of both PLX4720 (or PLX4320) and mAb225.28, are kept in culture as long as needed for monitoring whether and/or when secondary resistance occurs.

To analyze the mechanisms of action of combination treatment in primary and secondary resistances, cells are lysed for examining the changes in the level of total and activated signaling protein molecules by western blot as above. The significance of the difference in cell growth and the level of signaling molecules is analyzed using the Student T test.

Example 6

Human scFv-C21

Figures 5A, 5B:
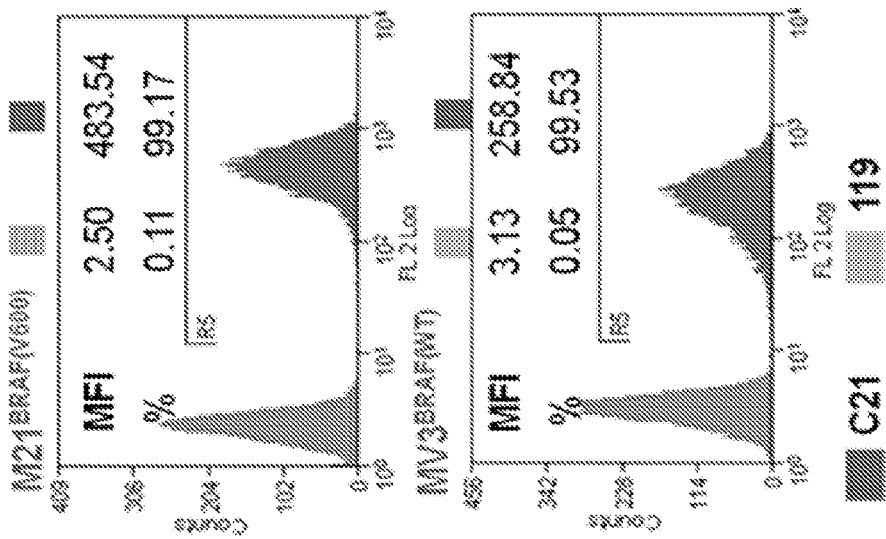
FIG. 5A to 5B. Broad reactivity of C21 with established and newly-derived human melanoma cell lines.

A fully human mAb, scFc-FcC21 was produced by combining the HMW-MAA (CSPG4)-specific single chain of variable regions of heavy and light chains (scFv) to a Fc portion of IgG1 at the DNA level. As a result, scFv-FcC21 (C21, see SEQ ID NOs: 3 and 4) is able to recognize a panel of established, or recently patient-derived, human melanoma cell lines containing BRAF$^{V600E}$ or wild type BRAF (BRAF$^{WT}$) (FIG. 5), and not a panel of normal human organ tissues (FIG. 6, see also Table 2 below).

TABLE 2

Lack of cross-reactivity of C21 with normal human organ tissues. A microarray of multiple normal human organ tissues (FDA Standard Frozen Tissue Array, Cat#: 902 US Biomax, Inc.) constructed from tissue cores obtained for 30 organs, with 3 individual donors per organ and triplicate cores per case, were stained with C21 (4 μg/mL). Frozen sections derived from cell lines M14/CSPG4 (CSPG4⁺) and M14 (CSPG4$^{neg}$) were simultaneously stained as positive and negative controls. Immunohistochemistry (IHC) results are indicated.

| Organ | Pathology Diagnosis | IHC Result |
|---|---|---|
| Lymph node | Normal lymph node tissue | negative |
| Skeletal muscle | Normal skeletal muscle tissue | negative |
| Prostate | Normal prostate tissue | negative |
| Kidney | Normal kidney tissue (partial autolysis of renal tubule) | negative |
| Liver | Normal liver tissue | negative |
| Lung | Normal lung tissue | negative |
| Stomach | Normal stomach tissue | negative |
| Esophagus | Normal esophagus tissue (skeletal muscle and smooth muscle) | negative |
| Heart | Normal cardiac muscle tissue | negative |
| Colon | Normal colon tissue | negative |
| Small intestine | Normal small intestine tissue | negative |
| Peripheral nerve | Normal peripheral nerve tissue | negative |
| Smooth muscle | Normal smooth muscle and gland tissue | negative |
| Cerebellum | Normal cerebellum tissue | negative |
| Cerebrum | Normal cerebrum tissue | negative |
| Spinal cord | Spinal cord tissue | negative |
| Ovary | Normal ovary tissue | negative |
| Pancreas | Normal pancreas tissue | negative |
| Salivary gland | Normal salivary gland tissue | negative |

TABLE 2-continued

Lack of cross-reactivity of C21 with normal human organ tissues. A microarray of multiple normal human organ tissues (FDA Standard Frozen Tissue Array, Cat#: 902 US Biomax, Inc.) constructed from tissue cores obtained for 30 organs, with 3 individual donors per organ and triplicate cores per case, were stained with C21 (4 µg/mL). Frozen sections derived from cell lines M14/CSPG4 (CSPG4+) and M14 (CSPG4$^{neg}$) were simultaneously stained as positive and negative controls. Immunohistochemistry (IHC) results are indicated.

| Organ | Pathology Diagnosis | IHC Result |
|---|---|---|
| Pituitary gland | Normal pituitary gland tissue | negative |
| Placenta | Normal placenta tissue | negative |
| Prostate | Normal prostate tissue | negative |
| Skin | Normal skin tissue | negative |
| Spinal cord | Normal spinal cord tissue (autocytolysis) | negative |
| Spleen | Normal spleen tissue | negative |
| Skeletal muscle | Normal skeletal muscle tissue | negative |
| Testis | Normal testis tissue | negative |
| Thymus | Normal thymus tissue | negative |
| Thyroid gland | Normal thyroid gland tissue | negative |
| Ureter | Normal ureter tissue | negative |
| Uterine cervix | Normal cervix tissue | negative |

Figure 7:
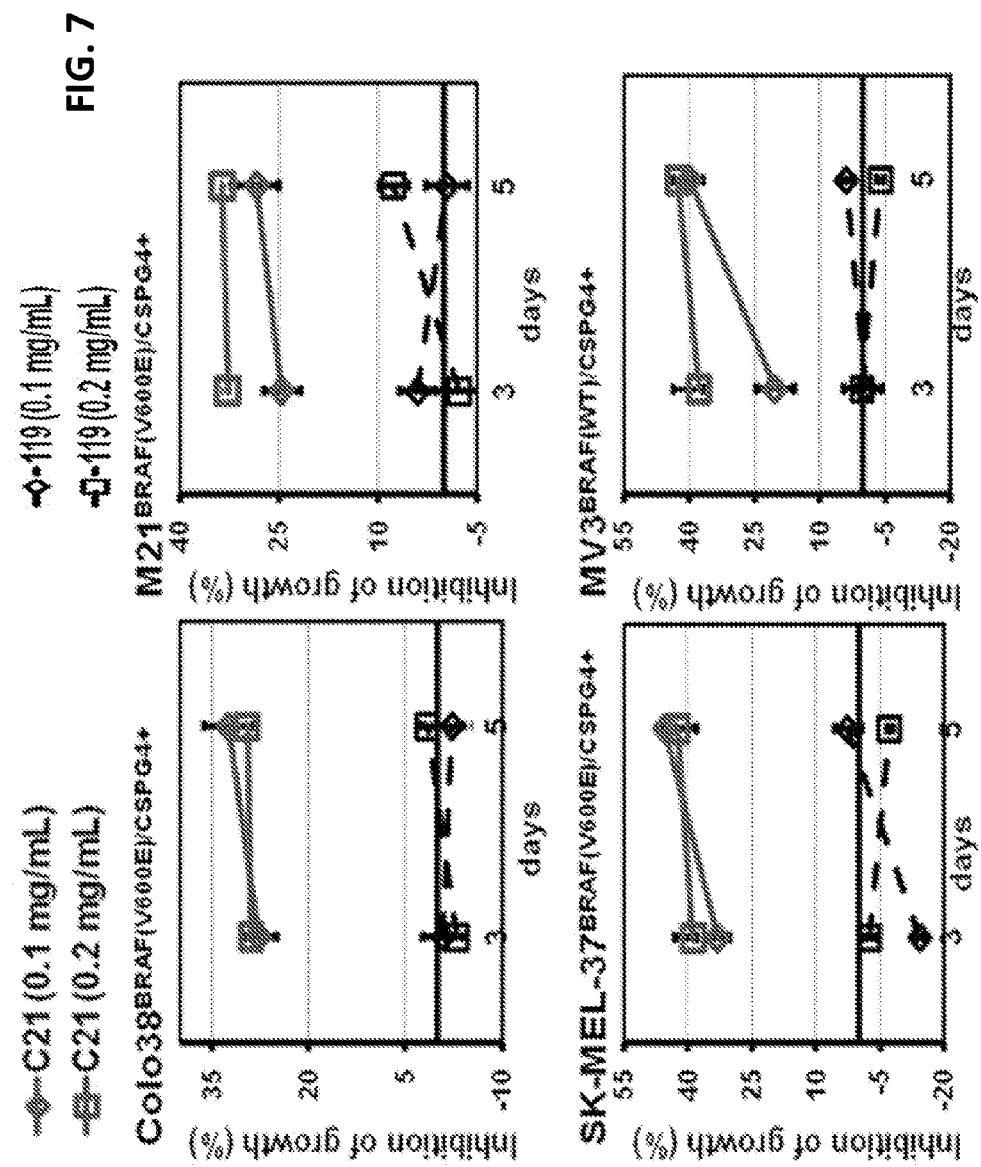
FIG. 7. Growth inhibition of melanoma cell lines by CSPG4-specific C21. The indicated cells were seeded in triplicate in 96-well plates ($2.5 \times 10^3$/well) and treated for 3, 5 days with C21 and 119 in RPMI 1640/1% FCS. Living cells were detected using MTT assays. The results are expressed as percent inhibition of cell growth, with untreated cells representing 100%. Mean values±SD were calculated from two independent experiments.

More importantly, C21 inhibited both BRAF$^{V600E}$ and BRAF$^{WT}$ melanoma cell growth in vitro (FIG. 7).

Example 7

Enhancement of Melanoma Response Magnitude to BRAF Inhibitor with C21

Figure 8:
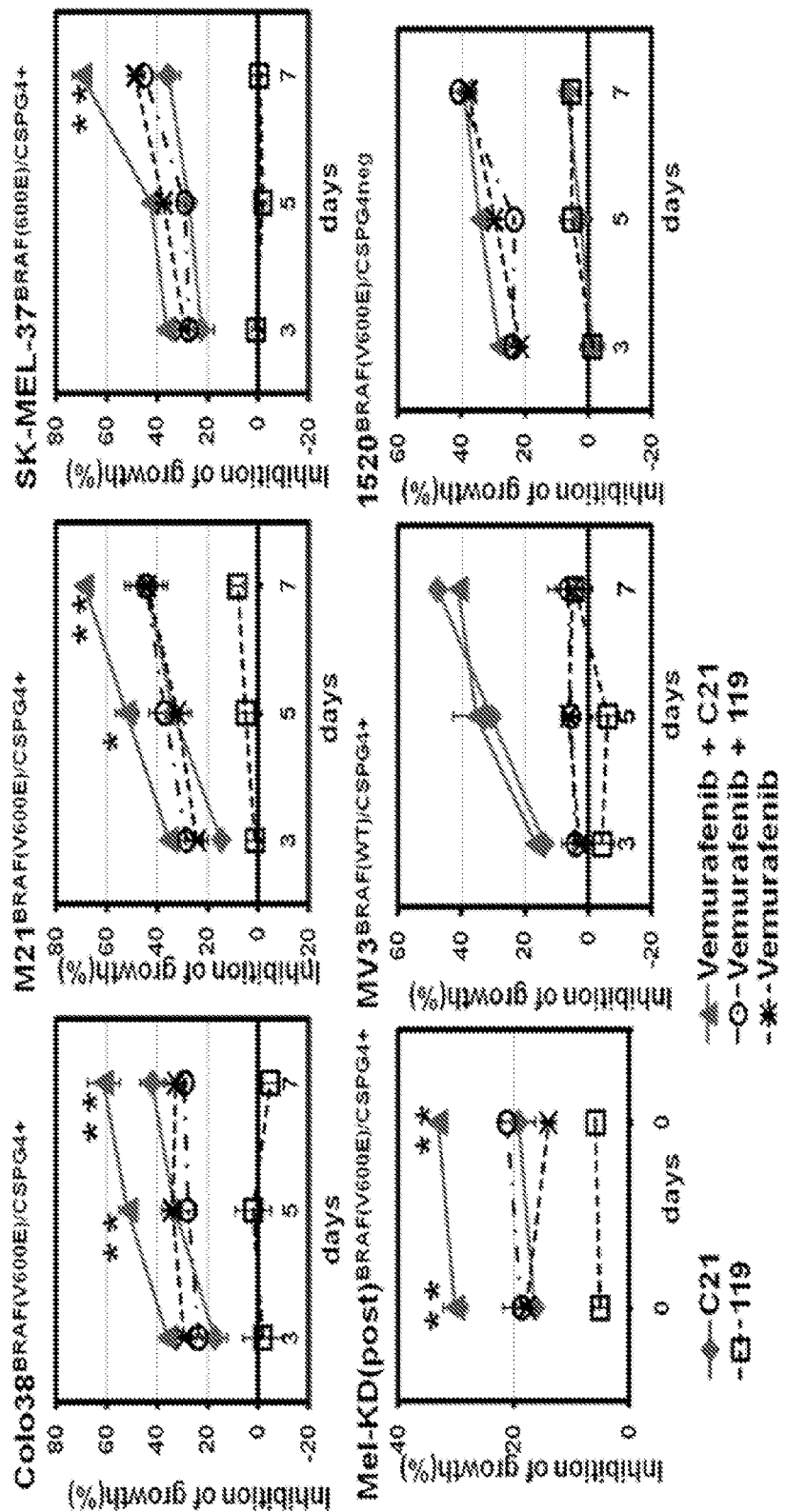
FIG. 8. The combination of vemurafenib and C21 suppresses the growth of various melanoma cell lines significantly better than either agent alone. $CSPG4^+$ Colo38, M21, and SK-MEL-37 cell lines containing BRAF(V600E) ($2.5 \times 10^3$/well) were seeded in triplicate in 96-well plates and treated with vemurafenib (500 nM), C21 (0.1 mg/mL), or both, in RPMI 1640/1.5% FCS for up to 7 d. Percent inhibition of cell growth was calculated, with untreated cells set at 100%. Mean values±SD were calculated from three independent experiments. Notably, vemurafenib did not affect the cell growth of $BRAF^{WT}$ MV3 cells, and C21 did not affect the growth of 1520 cells negative for CSPG4. * indicates p≤0.1; ** indicates p≤0.01.
Figure 9:
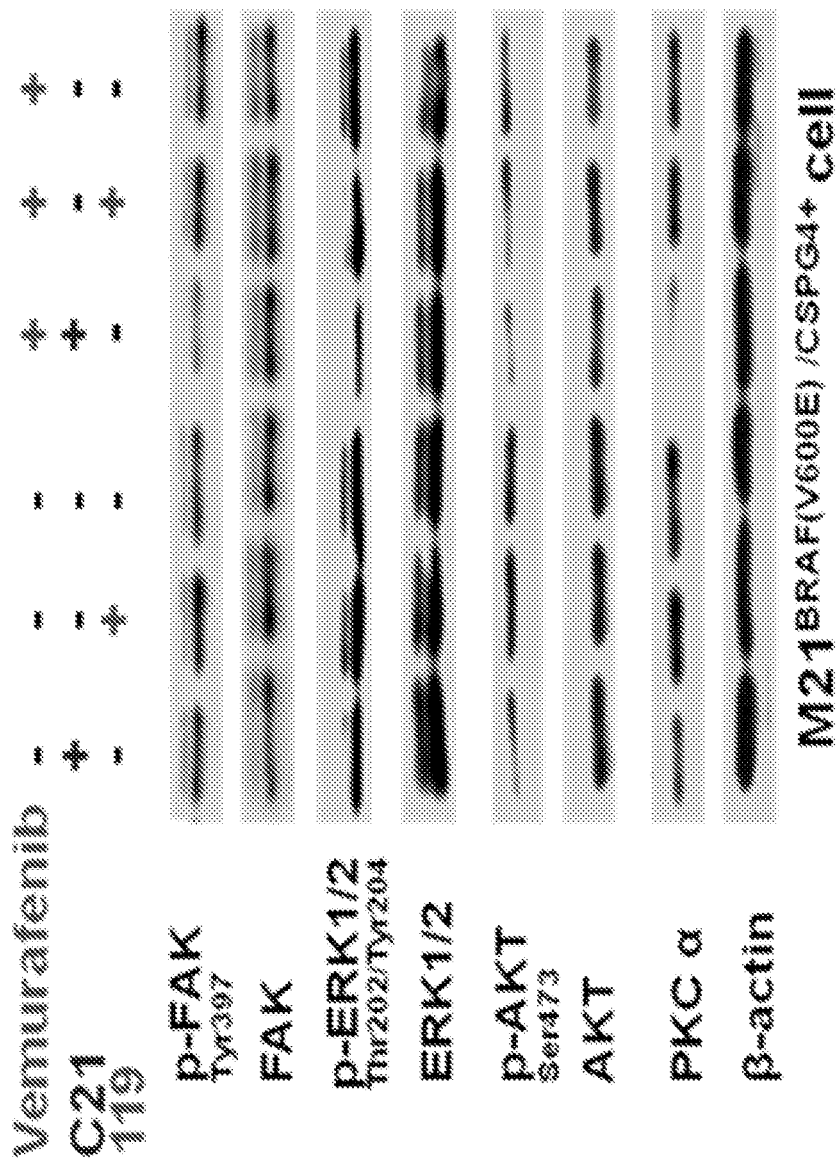
FIG. 9. Enhanced inhibition of the expression and activation of multiple signaling pathway proteins by vemurafenib and C21. Human melanoma $M21^{BRAF(V600E)/CSPG4+}$ cells were treated with vemurafenib, C21, or both in serum-free RPMI 1640 for 72 h. Cell lysates were then analyzed by immunoblot. Levels of p-FAK (Tyr397), FAK, p-ERK1/2 (Thr202/Tyr204), ERK1/2, p-AKT (Ser473), AKT, and PKCα were measured. Expression of β-actin was used as a loading control.
Figure 10A:
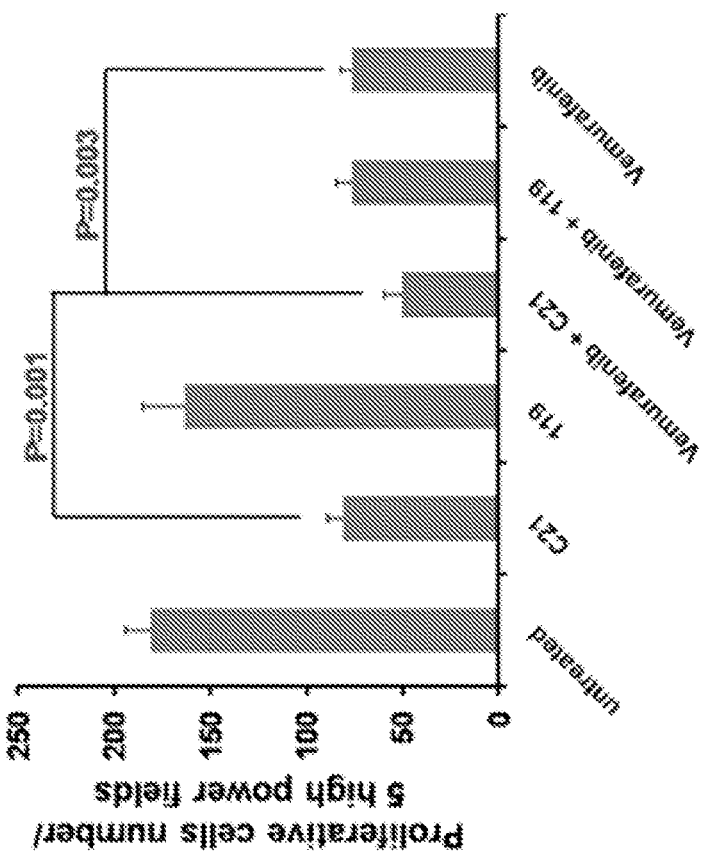
FIG. 10A-10C. Improved response magnitude for vemurafenib in vivo.
Figure 10B:
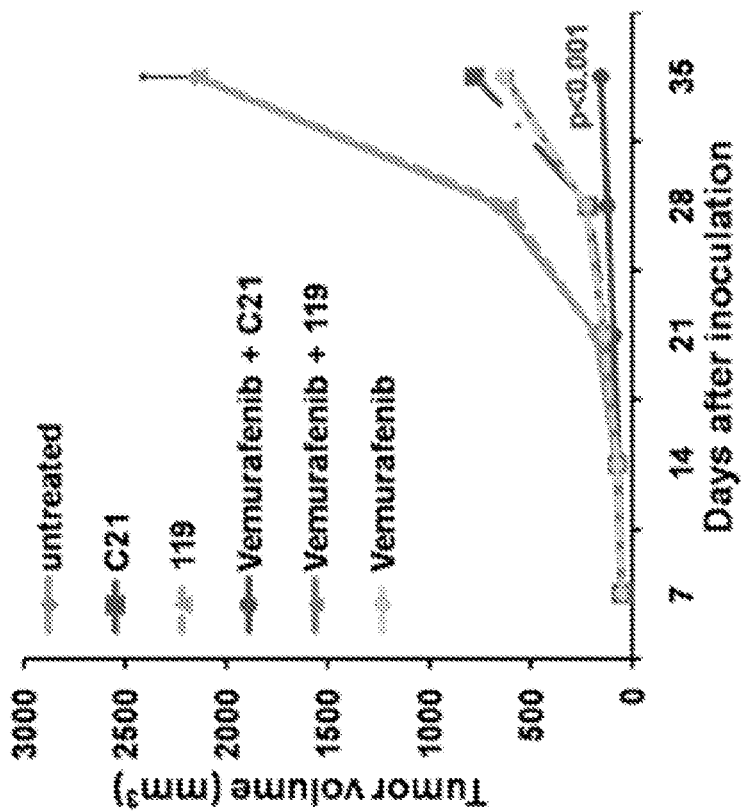
Figure 10C:
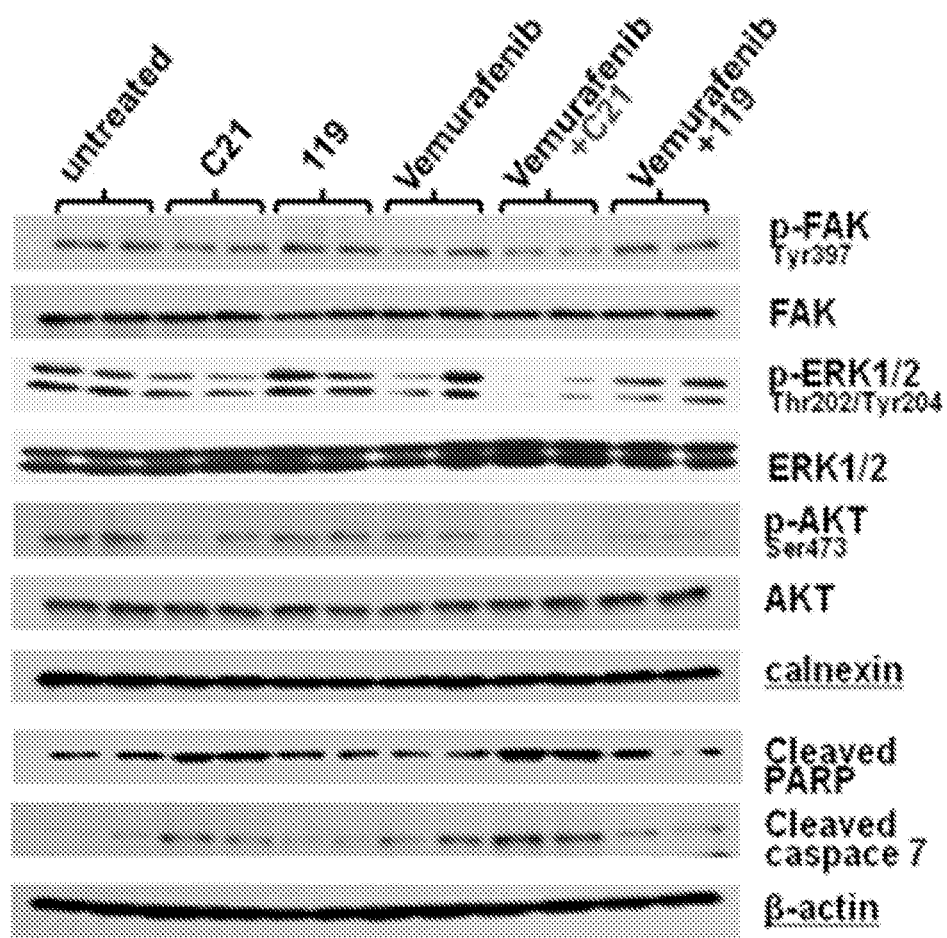
Figure 11:
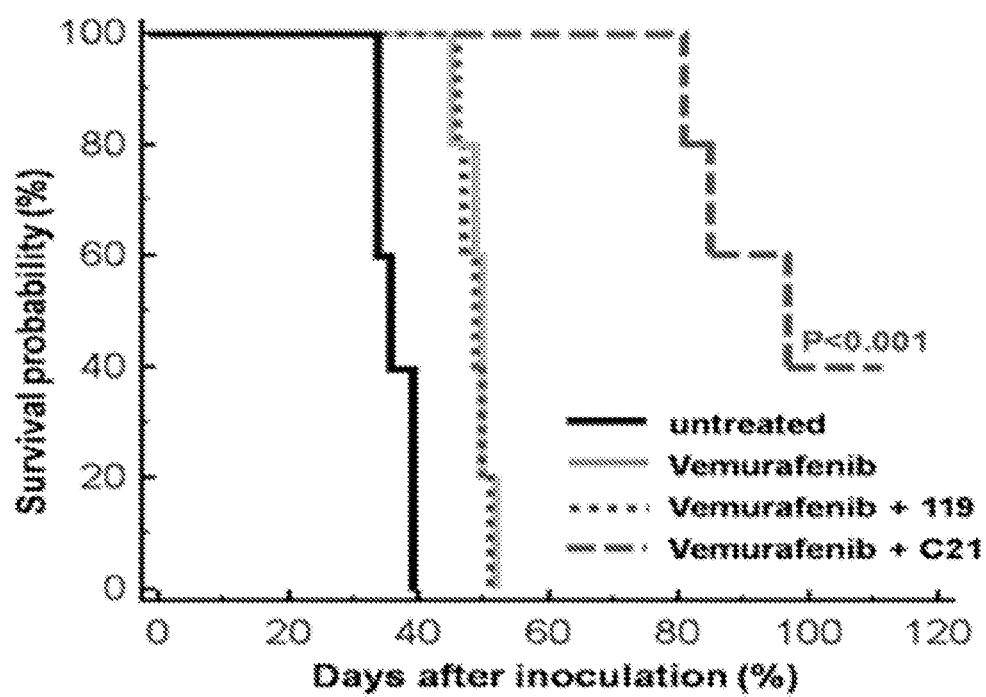
FIG. 11. Improved response duration for vemurafenib in vivo. Human melanoma $M21^{BRAF(V600E)/CSPG4+}$ cells ($2 \times 10^6$/mouse) were injected subcutaneously (s.c.) into 20 mice (day 0). By day 7, tumors were measurable, and mice were divided into four groups (5 mice/group) using a stratified randomization strategy. Mice received either vemurafenib, vemurafenib+C21, vemurafenib+119, or were untreated. Vemurafenib was delivered orally (25 mg/kg) twice a day for 13 days, while C21 or 119 were injected i.v. (1 mg/mouse) twice a week for 2 weeks. All mice were monitored for survival. The combination of vemurafenib+C21 significantly increased the survival of mice compared to mice treated with vemurafenib alone or vemurafenib+119.

The targeting of multiple signaling pathways simultaneously by vemurafenib and C21 could enhance the response magnitude of melanoma cells containing the BRAF$^{V600E}$ mutation. Correspondingly, FIG. 8 shows that a combination of vemurafenib (PLX4032, ChemieTek) and C21 was significantly stronger than either agent alone in inhibiting the growth of both BRAF$^{V600E}$ and CSPG4 positive (BRAF (V600E)/CSPG4$^+$) melanoma cells, including established cell lines and a newly isolated cell line from a patient indicated as Mel-KD (post Vemurafenib treatment). The enhanced inhibition was both BRAF$^{V600E}$- and CSPG4-dependent, since it was not associated with BRAF(V600E)/CSPG4$^{neg}$ (1520), or BRAF(WT)/CSPG4$^+$ (MV3) melanoma cell lines (FIG. 8). Indeed, the strongest inhibition of cell growth mediated by vemurafenib and C21 was attributed to an enhanced down-regulation of FAK, ERK and AKT activation and PKCα expression compared to either agent alone (FIG. 9). Correspondingly, the combination of vemurafenib and C21 was also significantly stronger than either agent alone in inhibiting the growth of M21$^{BRAF(V600E)/CSPG4+}$-derived tumor xenografts in vivo (FIG. 10). Moreover, C21 was able to increase the response duration of vemurafenib in vivo by prolonging the survival of mice bearing human melanoma BRAF(V600E)/CSPG4$^+$ xenografts, compared to xenografted treated with vemurafenib alone (FIG. 11).

Example 8

Enhanced Response Duration in Melanoma Cells Treated with BRAF Inhibitor

Figure 12:
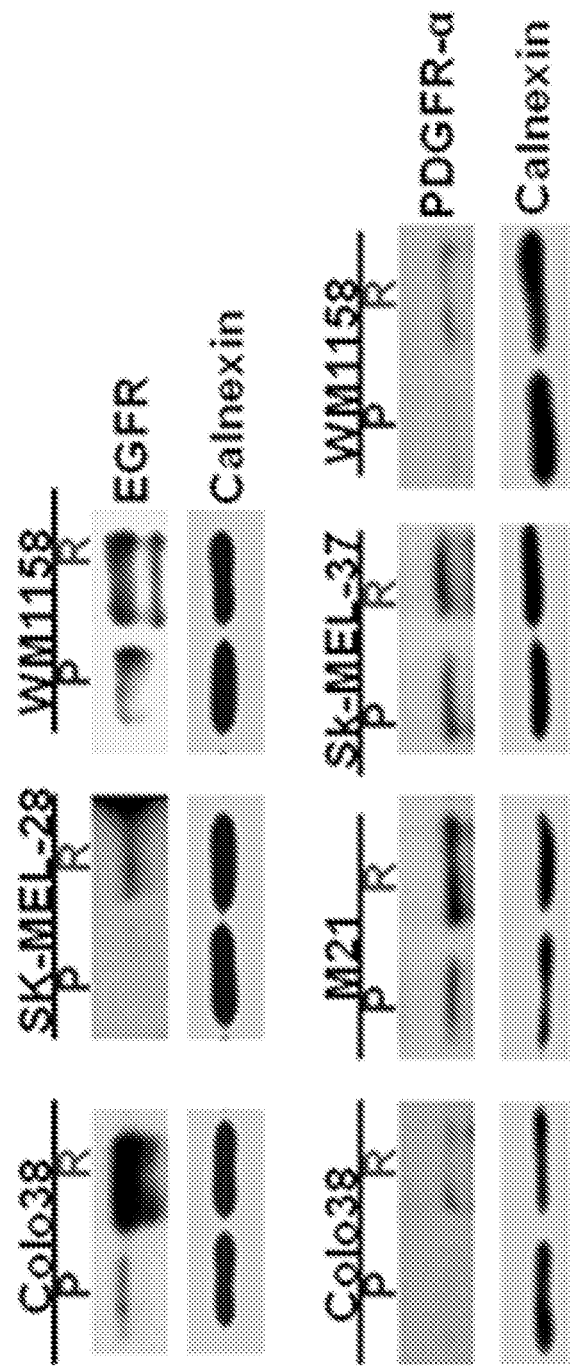
FIG. 12. Increased expression of EGFR and PDGFR-α in melanoma cell lines$^{BRAF(V600E)}$ resistant to vemurafenib (R) compared to parental (P) cell lines. Cell lysates of the indicated cell lines harboring the BRAF V600E mutation were analyzed for expression of EGFR and PDGFRα by immunoblotting. Calnexin was used as a loading control.
Figure 13:
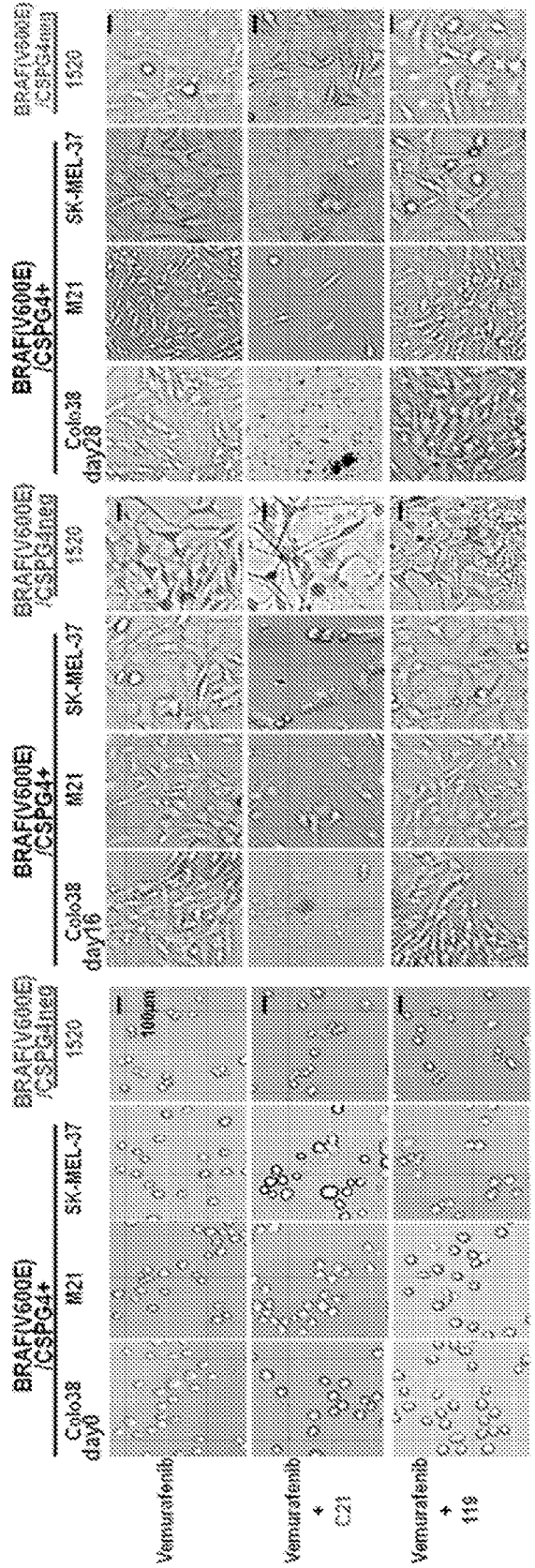
FIG. 13. Prevention/delay of acquired resistance of melanoma cells to vemurafenib. Melanoma cells were seeded in 6-well plates ($2.5 \times 10^4$ cells/well) containing 2 ml/well RPMI 1640/10% FCS. Cells were treated with: i) vemurafenib, ii) vemurafenib+C21, or iii) vemurafenib+119, with the dose of vemurafenib used for each treatment gradually increasing as indicated in Table 2, while the concentration of the antibodies (0.1 mg/mL) remained constant. Cells received fresh growth medium every 4 days containing the appropriate treatment concentrations, for 28 days. Cells in randomly selected fields were photographed at different timepoints using a Zeiss Inverted Fluorescence Microscope

It was determined that administration of C21 could prevent/delay acquired resistance by melanoma cells to a BRAF inhibitor by down-regulating activation of EGFR and PDG-FRα, both of which were found to be up-regulated in BRAF inhibitor-resistant cell lines (FIG. 12). In addition, the results presented in FIG. 13 evidences that treatment with C21 delayed resistance to vemurafenib up to 28 days in vitro, at which point the rate of cell growth was unaffected by the presence or absence of vemurafenib (10 µM) in the absence of C21. This prevention/delay was HMW-MAA (CSPG4)-specific, since C21 did not delay the onset of acquired resistance to vemurafenib in melanoma cell line, 1520, which is positive for BRAF$^{V600E}$, yet negative for HMW-MAA (CSPG4) expression. The timetable and dosages of vemurafenib and C21 used in is shown in the table below.

TABLE 3

The timeline and dosages of Vemurafenib and C21 used for in vitro treatment of melanoma cells.

| Treatment timeline (days) | Vemurafenib (nM) | Vemurafenib (nM) + C21 (mg/mL) | Vemurafenib (nM) + 119 (mg/mL) |
|---|---|---|---|
| 0 | 500 | 500 + 0.1 | 500 + 0.1 |
| 4 | 1,000 | 1,000 + 0.1 | 1,000 + 0.1 |
| 8 | 2,000 | 2,000 + 0.1 | 2,000 + 0.1 |
| 16 | 5,000 | 5,000 + 0.1 | 5,000 + 0.1 |
| 28 | 10,000 | 10,000 + 0.1 | 10,000 + 0.1 |

Example 6

BRAF-I and Anti-CSPG4 Antibody have a Synergistic Effect in Suppressing In Vivo Growth of V600E Mutated Melanoma Xenograft and Prolongation of Survival of the Tumor-Engrafted Mice The combination therapy of BRAF-I and anti-CSPG4 mAb 225.28 is significantly more effective than either agent alone in inhibiting in vivo growth of M21$^{V600E}$ cell line-derived tumor xenograft in immunodeficient mice. Therefore, to validate the in vivo result of tumor growth control an additional study is performed. The effect of combination therapy in prolongation of survival of mice engrafted with M21$^{V600E}$ cell line-derived tumor is determined.

Human melanoma cell line M21$^{V600E}$ (M21), at the dose of 2×10$^6$ cells/per mouse, which gives 100% tumor incidence within 1 week, is used to establish the primary melanoma tumor model. M21 cells are injected s.c. in 25 SCID mice. Tumor growth is monitored twice weekly by digital calipers. Tumor-bearing mice are divided by stratified randomization into 5 groups of 5 mice each. Mice in group 1 (PLX4720 or PLX4320) are treated with PLX4720 (or PLX4320, respectively). Mice in group 2 (mAb 225.28) are treated with mAb 225.28. Mice in group 3 (combination-PLX4720+ mAb225.28 or combination PLX4320+mAb225.28) are treated with PLX4720 (or PLX4320) and mAb 225.28. Mice in group 4 (PLX4720+isotype control or PLX4320+isotype control) are treated with PLX4720 (or PLX4320) and isotype control mAb F3-C25. Mice in group 5 (control) are left untreated as a reference for the natural course of the disease. All mAb (100 µg/mouse) are administered i.v., twice weekly. PLX4720 (or PLX4320) is given orally at 75 mg/kg, twice daily. This dose of BRAF-I is chosen since it achieved complete response on a V600E mutated cell line-derived xenogratf mouse model. All treatment is initiated on day 7 of post tumor cell inoculation and continued until the diameter of primary tumor (in the control group), reaches 1.5 cm or mice are moribund (end point), at which all mice are sacrificed.

To investigate the mechanisms of action underlying the effects on cell growth, migration and apoptosis, tumors are collected at the time of sacrifice, and treated as described above. The tumors are lysed to examine the changes in the level of total and activated signaling protein molecules, such as FAK, RAS, BRAF, ERK1/2, PI3, AKT, PKCα by Western blot. In addition, immunohistochemical staining (IHC) of formalin fixed and paraffin embedded (FFPE) tissue sections for proliferative and apoptotic cells are performed.

Mice treated with the combination therapy have prolonged survival. A total of 40 SCID mice are established with M21$^{V600E}$ cell line-derived tumor model as detailed above. Mice are divided into 5 groups of 10 mice each. Mice in group 1 (PLX4720 or PLX4320) are treated with PLX4720 (or PLX4320, respectively). Mice in group 2 (mAb 225.28) are treated with mAb 225.28. Mice in group 3 (PLX4720+ mAb225.28 or PLX4320+mAb225.28) are treated with PLX4720 (or PLX4320) and mAb 225.28. Mice in group 4 (PLX4720+isotype control or PLX4320+mAb228.25) are treated with PLX4720 (or PLX4320) and isotype control mAb F3-C25. Mice in group 5 (control) are left untreated. The treatment regimen is as described above, but the end point is survival, i.e., individual mouse in any group is sacrificed if the diameter of primary tumor reaches 1.5 cm or a mouse becomes moribund. All treatment is initiated on day 7 of post tumor cell inoculation and continues until the first mouse is sacrificed. The treatment period is up to one year. A Student's t test is used to compare tumor volumes, proliferative cells, apoptotic cells, signaling molecules between groups. If necessary, non-parametric Mann-Whitney and Kruskal-Wallis tests are applied when deviation from normality is significant. Group sizes of 10 mice are based on 80% power. A p-value of less than 0.05 is considered statistically significant in these analyses. The log rank test will be used for analysis of the survival data.

It will be apparent that the precise details of the methods or compositions described may be varied or modified without departing from the spirit of the described invention. We claim all such modifications and variations that fall within the scope and spirit of the claims below.

The invention claimed is:

1. A method of treating a subject diagnosed with a tumor, comprising administering to the subject (1) a therapeutically effective amount of a monoclonal antibody or antigen binding fragment thereof that specifically binds high molecular weight melanoma associated antigen (HMW-MAA); and (2) a therapeutically effective amount of a BRAF inhibitor, thereby treating the tumor in the subject, wherein the tumor expresses a mutated BRAF, wherein:

the tumor is melanoma;
the BRAF inhibitor is PLX4032 or PLX4720; and
the monoclonal antibody, or antigen binding fragment thereof comprises a heavy chain variable domain and a light chain variable domain, wherein the heavy chain variable domain of the monoclonal antibody comprises the amino acid sequence set forth as amino acids 26-33 of SEQ ID NO: 3, amino acids 51-58 of SEQ ID NO: 3, and amino acids 97-103 of SEQ ID NO: 3 and the light chain variable domain of the antibody comprises the amino acid sequence set forth as amino acids 27-32of SEQ ID NO: 4, amino acids 50-52 of SEQ ID NO: 4, and amino acids 89-97 of SEQ ID NO: 4.

2. The method of claim 1, wherein:
BRAF inhibitor is PLX4032.

3. The method of claim 2, wherein the subject has primary or secondary resistance to PLX4032.

4. The method of claim 2, wherein the genome of cells in the tumor comprises a BRAF mutation.

5. The method of claim 3, wherein the BRAF mutation is a V600E mutation.

6. The method of claim 2, wherein treating the tumor comprises inhibiting the growth of the tumor.

7. The method of claim 1, wherein treating the tumor comprises decreasing the metastasis of the tumor.

8. The method of claim 1, wherein the subject is human.

9. The method of claim 1, wherein the melanoma is superficial spreading melanoma, nodular melanoma, acral lentiginous melanoma, lentiginous malignant melanoma, or mucosal lentinginous melanoma.

10. The method of claim 1, wherein the melanoma is a cutaneous melanoma, an intraocular melanoma, a clear-cells sarcoma of the soft tissues, or an extracutaneous melanoma.

11. The method of claim 1, further comprising administering one or more additional chemotherapeutic agents.

12. The method of claim 1, wherein the genome of cells in the tumor comprises a BRAF mutation.

13. The method of claim 12, wherein the BRAF mutation is a V600E mutation.

14. The method of claim 12, wherein the BRAF mutation is R4621, 1463S, G464E, G464V, G466A, G466E, G466V, G469A, G469E, N581S, E585K, D594V, F595L, G596R, L597V, T5991, V600D, V600E, V600K, V600R, K601E or A728V mutation.

15. The method of claim 13, further comprising detecting a V600E BRAF mutation in a sample from the subject, wherein the sample comprises cells from the tumor.

16. The method of claim 1, comprising administering to the subject a therapeutically effective amount of the antigen binding fragment of a monoclonal antibody that specifically binds HMW-MAA.

17. The method of claim 1, wherein treating the tumor comprises inhibiting the growth of the tumor.

* * * * *